US005480387A

United States Patent [19]
Gabriel et al.

[11] Patent Number: 5,480,387
[45] Date of Patent: Jan. 2, 1996

[54] INJECTION DEVICE

[75] Inventors: Jochen Gabriel, Stuttgart; Herbert Bechtold, Ehningen, both of Germany

[73] Assignee: Medico Development Investment Company, Zurich, Switzerland

[21] Appl. No.: 295,143

[22] Filed: Aug. 24, 1994

Related U.S. Application Data

[63] Continuation of Ser. No. 152,249, Nov. 12, 1993, abandoned, which is a continuation of Ser. No. 918,838, Jul. 22, 1992, abandoned.

[30] Foreign Application Priority Data

Jul. 24, 1991 [DE] Germany ............ 41 24 536.9

[51] Int. Cl.$^6$ .................................................. A61M 5/20
[52] U.S. Cl. ..................... 604/134; 604/136; 604/138; 604/156; 604/232
[58] Field of Search ............ 604/187, 206–211, 604/218, 199, 117, 232, 131, 134, 135, 136, 220, 191, 68, 71, 72, 137, 138, 139, 156, 157, 188

[56] References Cited

U.S. PATENT DOCUMENTS

| | | | |
|---|---|---|---|
| 2,565,081 | 8/1951 | Maynes. | |
| 4,498,904 | 2/1985 | Turner et al.. | |
| 4,592,745 | 6/1986 | Rex et al. | 604/211 |
| 4,643,721 | 2/1987 | Brunet | 604/191 |
| 4,865,591 | 9/1989 | Sams | 604/186 |
| 4,883,472 | 11/1989 | Michel | 604/208 |
| 4,973,318 | 11/1990 | Holm et al.. | |
| 5,017,190 | 5/1991 | Simon et al. | 604/207 |
| 5,042,977 | 8/1991 | Bechtold et al.. | |
| 5,085,641 | 2/1992 | Sarnoff et al. | 604/134 |
| 5,085,642 | 2/1992 | Sarnoff et al. | 604/134 |
| 5,092,842 | 3/1992 | Bechtold et al.. | |
| 5,104,380 | 4/1992 | Holman et al. | 604/117 |
| 5,112,317 | 5/1992 | Michel | 604/208 |
| 5,114,406 | 5/1992 | Gabriel et al.. | |
| 5,176,643 | 1/1993 | Kramer et al. | 604/135 |

FOREIGN PATENT DOCUMENTS

| | | | |
|---|---|---|---|
| 0268191 | 11/1987 | European Pat. Off.. | |
| 0265876A2 | 5/1988 | European Pat. Off.. | |
| 0265876 | 5/1988 | European Pat. Off.. | |
| 0327910 | 8/1989 | European Pat. Off.. | |
| 7204481 | 4/1973 | Germany. | |
| 7638511 | 8/1977 | Germany. | |
| 7830153 | 10/1978 | Germany. | |
| 8326217 | 9/1983 | Germany. | |
| 0250467 | 10/1987 | Germany | 604/187 |
| 3638984C2 | 5/1988 | Germany. | |
| 3715340A1 | 11/1988 | Germany. | |
| 0273201 | 11/1989 | Germany | 604/187 |
| 0279174 | 5/1990 | Germany | 604/187 |
| 3914818 | 11/1990 | Germany. | |
| 4013769 | 10/1991 | Germany. | |
| 9200192 | 1/1992 | Germany. | |
| 8808724 | 11/1988 | WIPO. | |
| WO91/01153 | 2/1991 | WIPO. | |

Primary Examiner—C. Fred Rosenbaum
Assistant Examiner—V. Alexander
Attorney, Agent, or Firm—Frishauf, Holtz, Goodman, Langer & Chick

[57] ABSTRACT

An injection device (10) is adapted to receive a cartridge (11) holding injection fluid (12). This cartridge (11) is displaceable in the proximal direction in the injection device counter to the force of a resetting spring (157). An adjustable-length tappet (80) is biased in the proximal direction by a spring (53), is displaceable in the injection device between a proximal end position and a distal end position, and has a threaded spindle (19) which is guided in the thread (17) of an adjusting member (15), serves to act upon a plunger (23) provided in the cartridge (11), and has a guide member (67) associated with it; the guide member is connected to it in a manner fixed against relative rotation but axially freely displaceably. This guide member (67) is rotatable relative to the housing (100) of the injection device (10) in the distal end position of the tappet (80), but not in the proximal end position thereof.

23 Claims, 15 Drawing Sheets

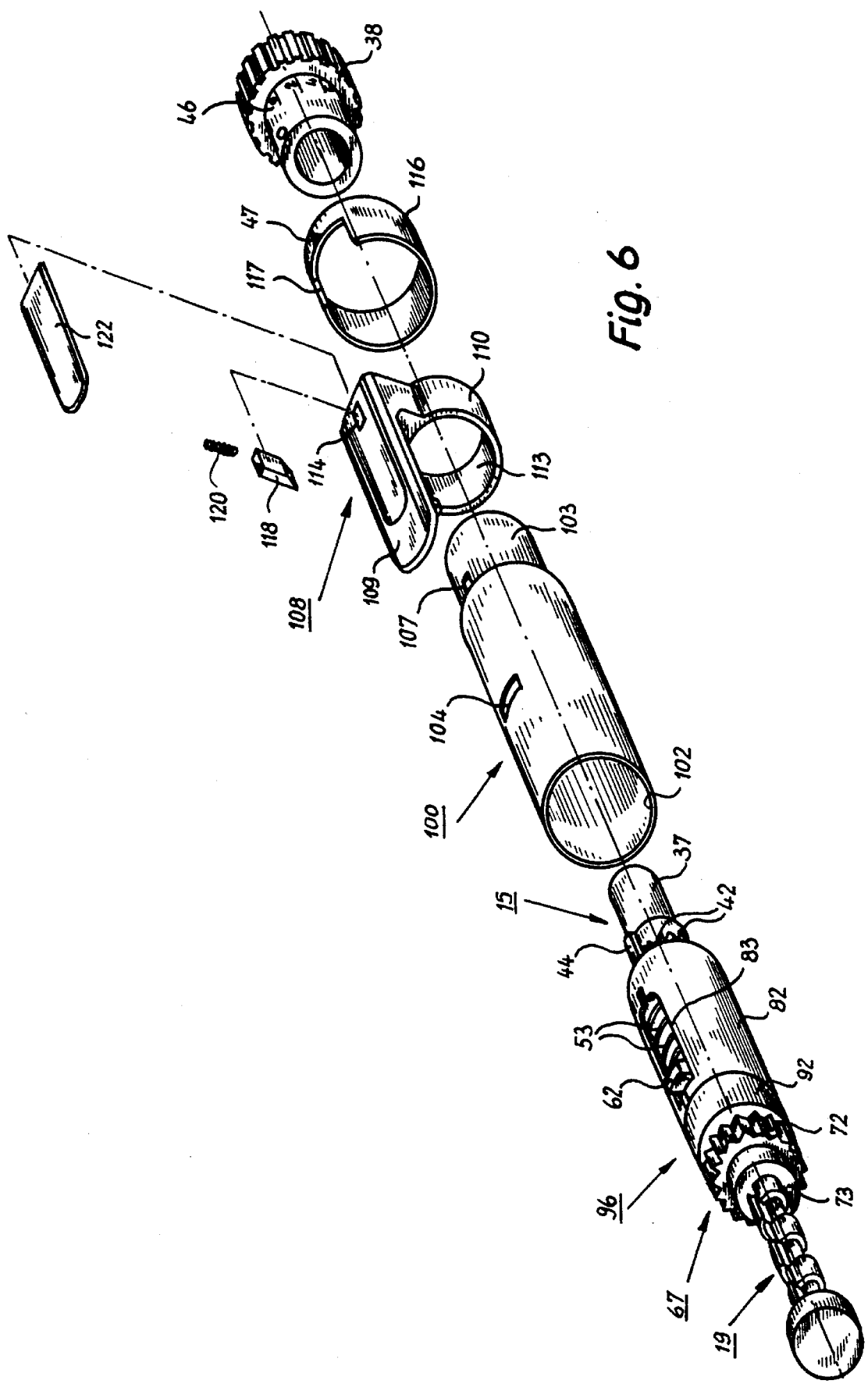

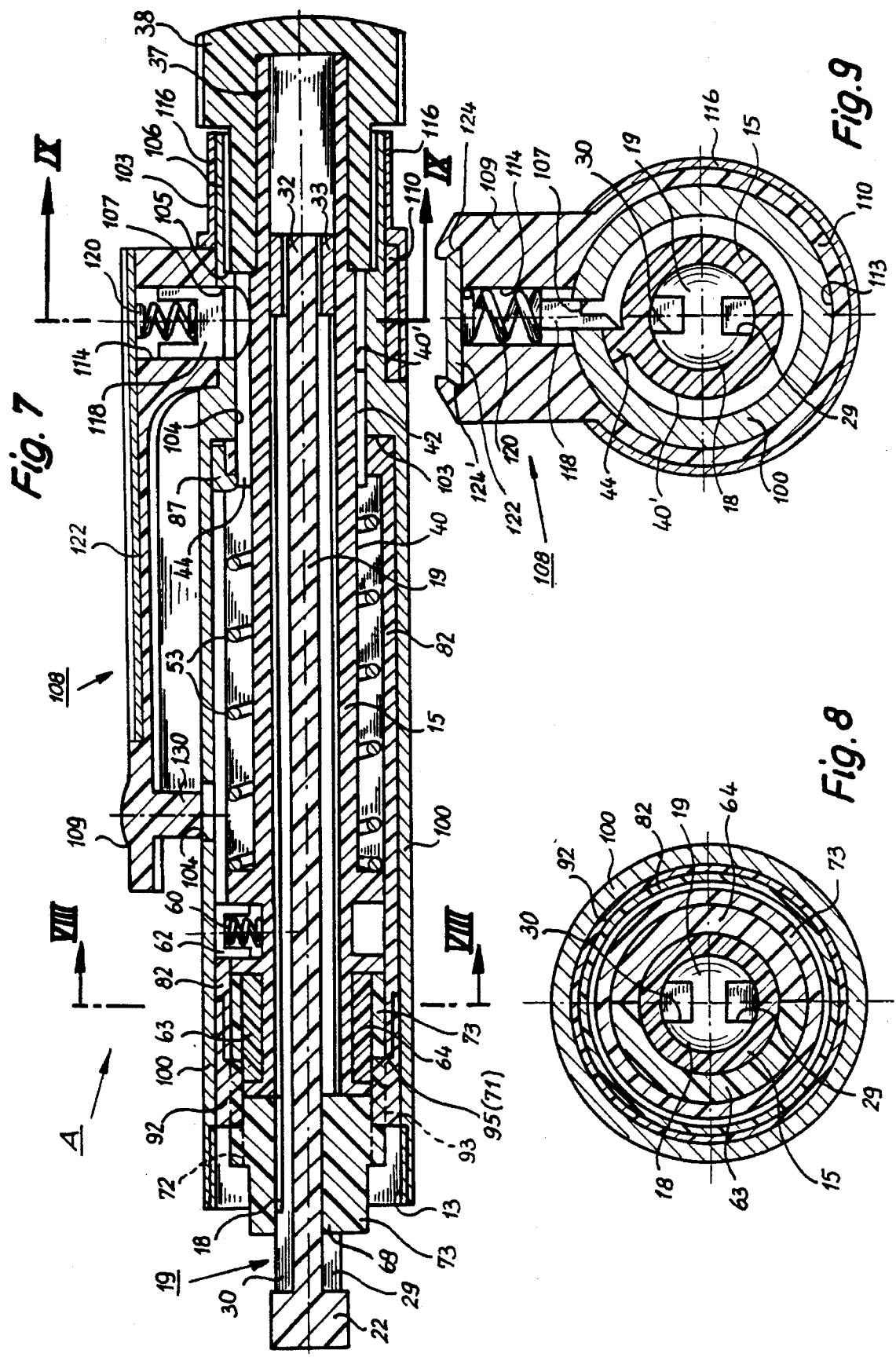

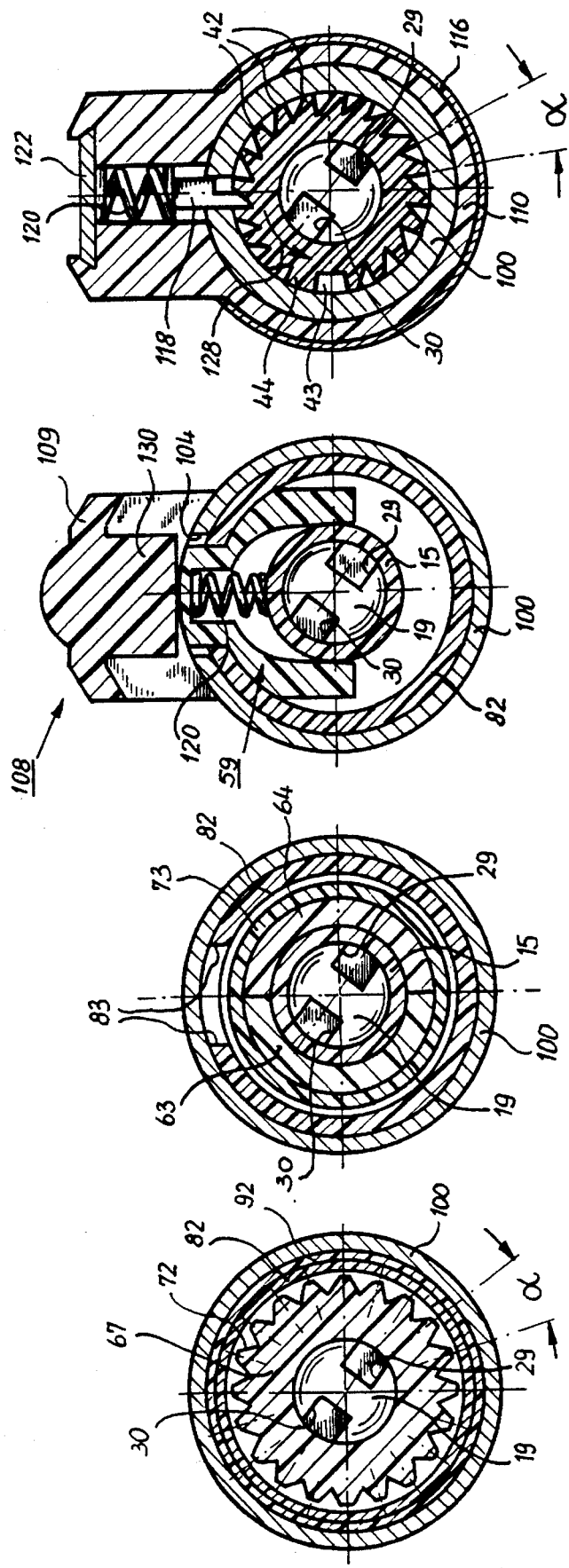

INJECTION DEVICE

This application is a Continuation of application Ser. No. 08/152,249, filed Nov. 12, 1993, now abandoned which is a continuation of application Ser. No. 07/918,838, filed Jul. 22, 1992, also abandoned.

FIELD OF THE INVENTION

The invention relates to an injection device for receiving a cartridge with enough injection fluid usually for multiple injections; in it, the cartridge can be shifted proximally counter to the force of a biasing spring, and there is a tappet of adjustable length that is acted upon proximally by a spring and can be shifted in the injection device between a proximal end position and a distal end position and has a threaded spindle guided in the thread of an adjusting member, for action upon a plunger provided in the cartridge; a guide member is associated with said threaded spindle and is connected thereto in a manner secured against relative rotation but axially displaceably.

BACKGROUND OF THE INVENTION

One such injection device is known from European Patent Document 0 349 592 B1. This known injection device makes for easy use but requires not inconsiderable thought on the part of the user, and the user must be trained in its use.

SUMMARY OF THE INVENTION

An object of the invention is to provide an improved injection device.

Briefly, in accordance with one aspect of the invention, an injection device is provided for holding a cartridge containing a quantity of injection fluid typically adequate for multiple injections. The cartridge is displaceable in a proximal direction in the injection device counter to the force of a resetting spring. An adjustable-length tappet is acted upon in the proximal direction by a spring, such tappet being displaceable in the injection device between a proximal end position and a distal end position and it includes a threaded spindle, guided in thread of an adjusting member for action upon a plunger provided in the cartridge. A guide member is associated with the threaded spindle, and is coupled thereto in a manner fixed against relative rotation but axially displaceably. The guide member is rotatable relative to the housing of the injection device in the distal end position of the tappet, but not in the proximal end position thereof.

As a result, the actual injection process, in other words the injecting device of fluid, cannot proceed until the needle has already penetrated the skin. After the injection, the injection device is in a position that does not require resetting processes on the part of the user. This makes for simpler function.

Rotating the adjusting member relative to the guide member in the proximal end position of the tappet—for the sake of injecting injection fluid—can be done manually, but preferably a spring that can be cocked by rotating the adjusting member is provided between the housing and the adjusting member, and in the distal end position of the tappet a blocking device is provided, which enables such rotation of the adjusting member only in a certain direction and blocks rotation in the opposite direction. Accordingly, this spring can be cocked in the distal end position and can then relax in the proximal end position, in order to rotate the adjusting member relative to the guide member and to effect the injection of the injection fluid.

In accordance with another aspect of the invention, an injection device is provided for holding a cartridge containing a quantity of injection fluid typically adequate for multiple injections. The cartridge is displaceable in a proximal direction in the injection device counter to the force of a resetting spring. An adjustable-length tappet is acted upon in the proximal direction by a spring, such tappet being displaceable in the injection device between a proximal end position and a distal end position and including a threaded spindle, guided in thread of an adjusting member for action upon a plunger provided in the cartridge. A guide member is associated with the threaded spindle, and is coupled thereto in a manner fixed against relative rotation but axially displaceable. The guide member is adapted to act, during the proximal displacement of the cartridge taking place in the injection process, upon this cartridge, or a cartridge holder receiving it, directly and to displace it.

A positive displacement of the cartridge (and the needle connected to it, which in the process penetrates the flesh of the patient) is thus attained. This makes it possible to use the injection device for drawing blood prior to the injection as well, by using a so-called lancet syringe in accordance with German Patent Disclosure 38 42 317 A1.

Advantageously, the guide member is joined to the adjusting member rotatably but axially undisplaceably. This provides a predetermined axial position of the guide member relative to the adjusting member, which is practical for this kind of positive displacement of the cartridge (naturally, the cartridge may be disposed in a cartridge holder, and then that holder is displaced by the guide member).

Another aspect of the invention is directed to an injection device for holding a cartridge containing a quantity of injection fluid typically adequate for multiple injections. The cartridge is displaceable in a proximal direction in the injection device counter to the force of a resetting spring. An adjustable-length tappet is acted upon in the proximal direction by a spring, such tappet being displaceable in the injection device between a proximal end position and a distal end position and including a threaded spindle, guided in thread of an adjusting member for action upon a plunger provided in the cartridge. A guide member is associated with the threaded spindle, and is coupled thereto in a manner fixed against relative rotation but axially displaceably. The guide member is adapted to act, during the proximal displacement of the cartridge taking place in the injection process, upon this cartridge, or a cartridge holder receiving it, directly and to displace it. The guide member is rotatable relative to the housing of the injection device (10) in the distal end position of the tappet, but not in the proximal end position.

A positive displacement of the cartridge is thus achieved, coupled with an injection only when the injection needle has already penetrated the patient's flesh.

A further aspect of the invention is directed to an injection device for holding a cartridge containing a quantity of injection fluid typically adequate for multiple injections. The cartridge is displaceable in a proximal direction in the injection device counter to the force of a resetting spring. An adjustable-length tappet is acted upon in the proximal direction by a spring, such tappet being displaceable in the injection device between a proximal end position and a distal end position and it includes a threaded spindle, guided in thread of an adjusting member for action upon a plunger provided in the cartridge. A guide member is associated with the threaded spindle, and is coupled thereto in a manner fixed against relative rotation but axially displaceably. A setting member is provided for setting the injection dose in the distal end position. A scale enables reading the set dose. Means automatically expels, in the region of the proximal end position of the tappet, the previously set injection dose and resets the setting member to zero with respect to the scale.

BRIEF DESCRIPTION OF THE DRAWINGS

Further details and advantageous features of the invention will become apparent from the exemplary embodiment described below and shown in the following drawings.

FIG. 6 is a three-dimensional view of the element of FIGS. 4 and 5 together with further elements of the injection device prior to their assembly;

FIG. 7 is a longitudinal section through the assembled element of FIG. 6, which is used upon an injection for first injecting the needle into the body of the patient and then injecting the previously set dose; the element is in its uncocked basic position, as also shown in FIG. 17;

FIG. 8, a section taken along the line VIII—VIII of FIG. 7, but on a larger scale than FIG. 7, for the sake of making details clearer;

FIG. 9, a section taken along the line IX—IX of FIG. 7, but on a larger scale than FIG. 7, for the sake of making details clearer;

FIGS. 11–14 are sections taken along the lines XI—XI to XIV—XIV of FIG. 10;

DETAILED DESCRIPTION OF THE INVENTION

Figure 1:
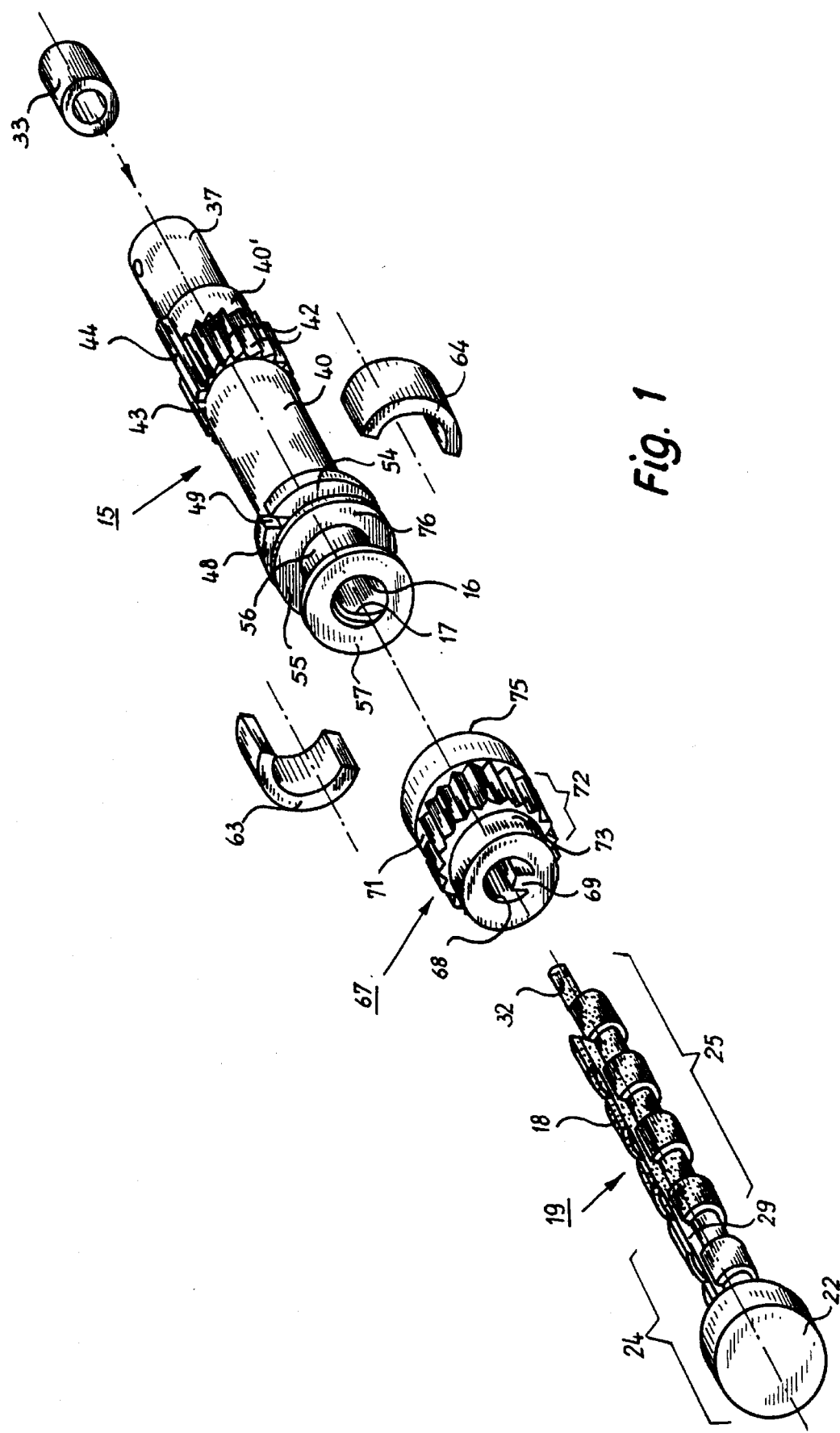
FIG. 1 is a three-dimensional view of internal elements of the injection device prior to their assembly.

In the following description, the terms proximal and distal are used in the conventional way in medicine; that is, proximal means oriented toward the patient and distal means oriented away from the patient. The terms left, right, top and bottom each refer to the applicable figure of the drawing.

Figure 16:
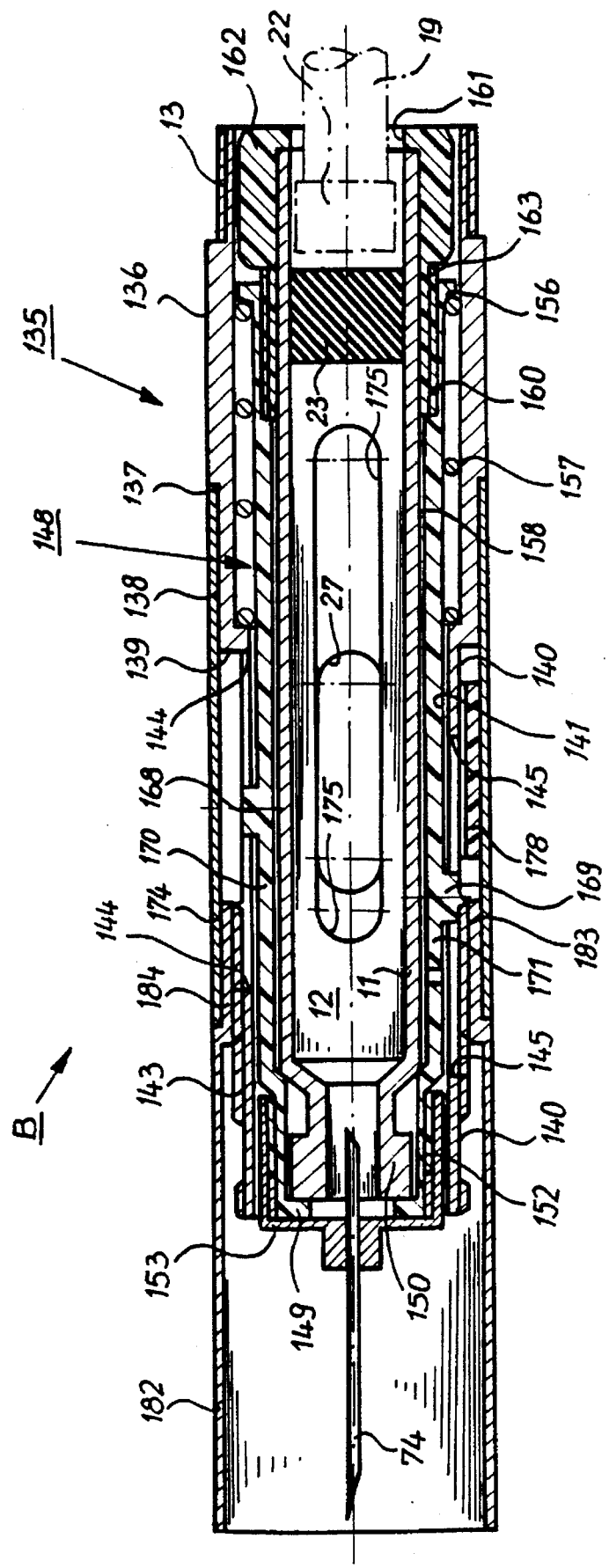
FIG. 16 is a longitudinal section through the parts of FIG. 15 in their assembled state.
Figure 17:
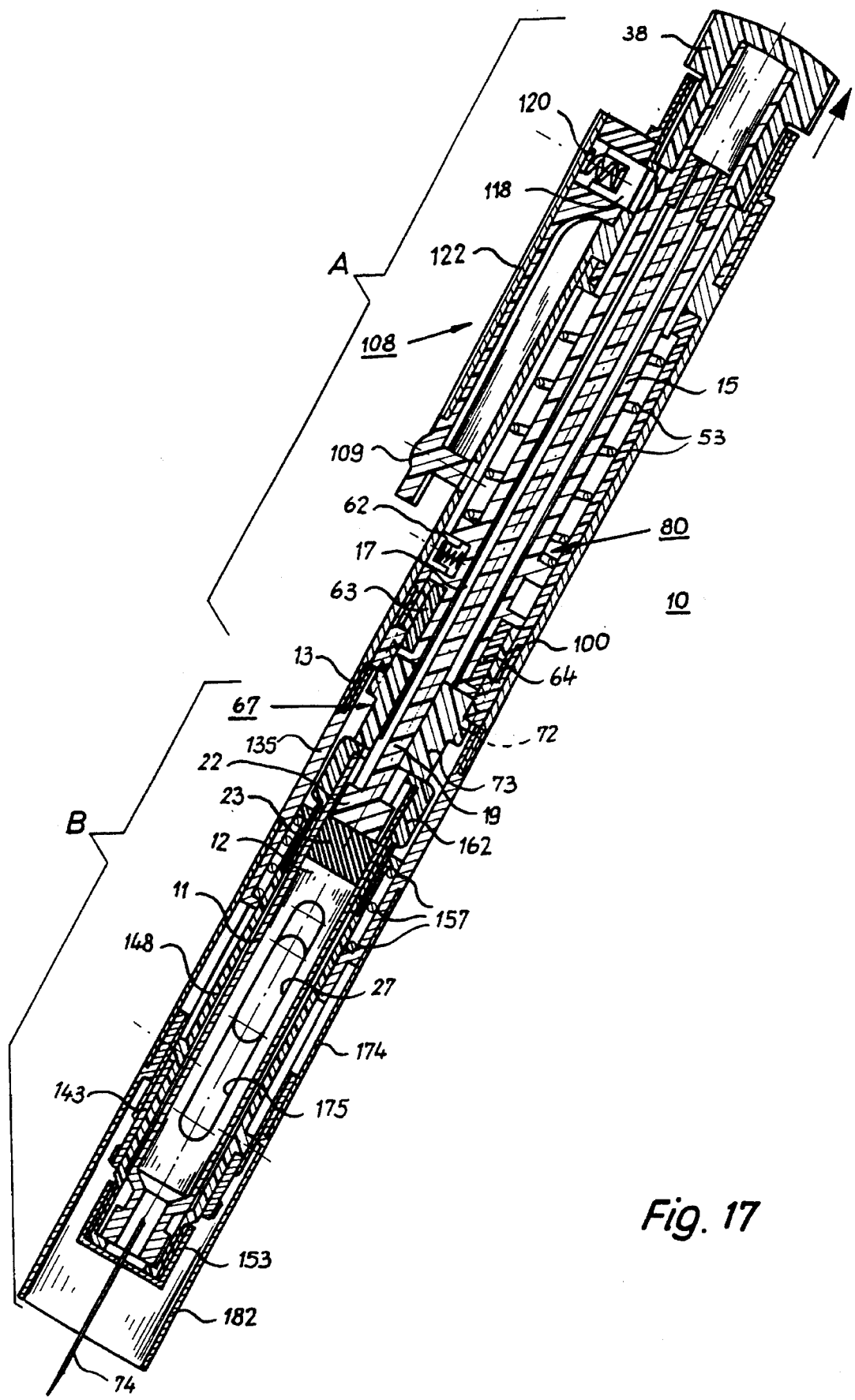
FIG. 17 is a complete view in longitudinal section of an injection device of the invention in its basic position.
Figure 18:
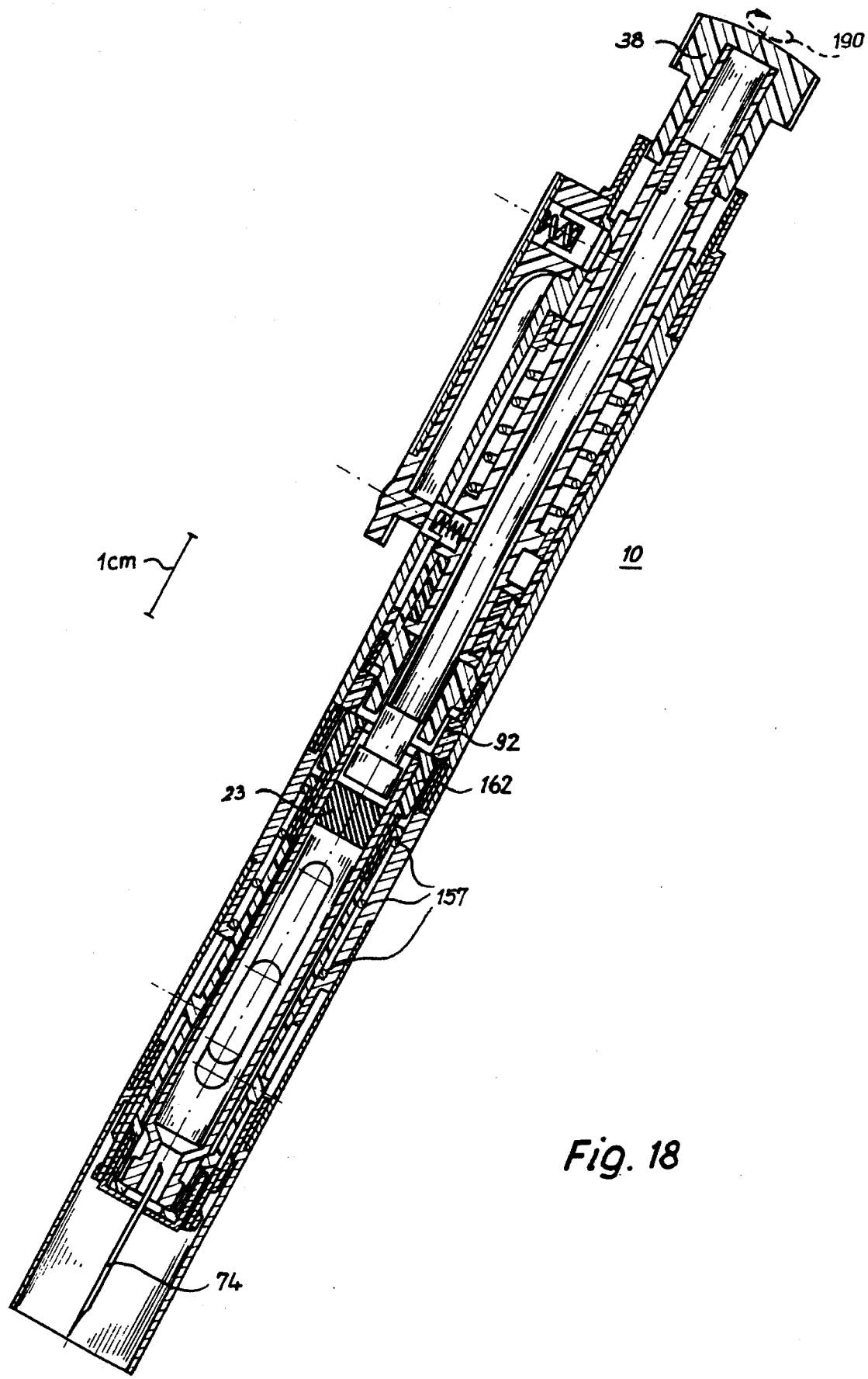
FIG. 18 is a complete view of the injection device of FIG. 17 in its cocked position and after an injection dose has been set; to illustrate the dimensional relationships, the length of 1 cm has been shown by way of example in FIG. 18.

FIGS. 17–20 show a preferred embodiment of a completely assembled injection device 10 according to the invention, in various positions during use. FIG. 18 shows one centimeter to serve as a scale. This scale also applies to FIG. 16 and FIGS. 19 and 20. The complete injection device is approximately the shape of an oversized fountain pen, and in its basic position in FIG. 17 it has a total length, measured from the needle point, of e.g. approximately 16.1 cm. This is supplemented with a cover cap (not shown) for the proximal injection device end with the injection needle, so that the total length may be approximately 17 cm. The diameter of the cylindrical part may be 1.6 cm, for example. In other words, the injection device is very easy to handle; as the following description will show, its use is also very simple and largely foolproof.

Since the drawings of FIGS. 17–20 are difficult to understand, the following discussion describes the injection device in terms of how it is assembled from its individual parts in the factory, which will make its structure and function substantially easier to understand.

The injection device 10 shown has a distal part A (FIG. 17), which serves to set the dose to be injected and to carry out the injection process, and it has a proximal part B that receives a cartridge (ampoule) 11 with the fluid 12 to be injected. The parts A and B are screwed together by means of a thread 13 and consequently can be unscrewed from one another, for instance in order to replace an empty cartridge 11 whose contents 12 have been used with a full cartridge, and to adjust the injection device accordingly for a new cartridge.

The structure of part A will first be described below in conjunction with FIGS. 1–14, and then the structure of part B in conjunction with FIGS. 15 and 16.

Part A (FIGS. 1–14)

Figure 5:
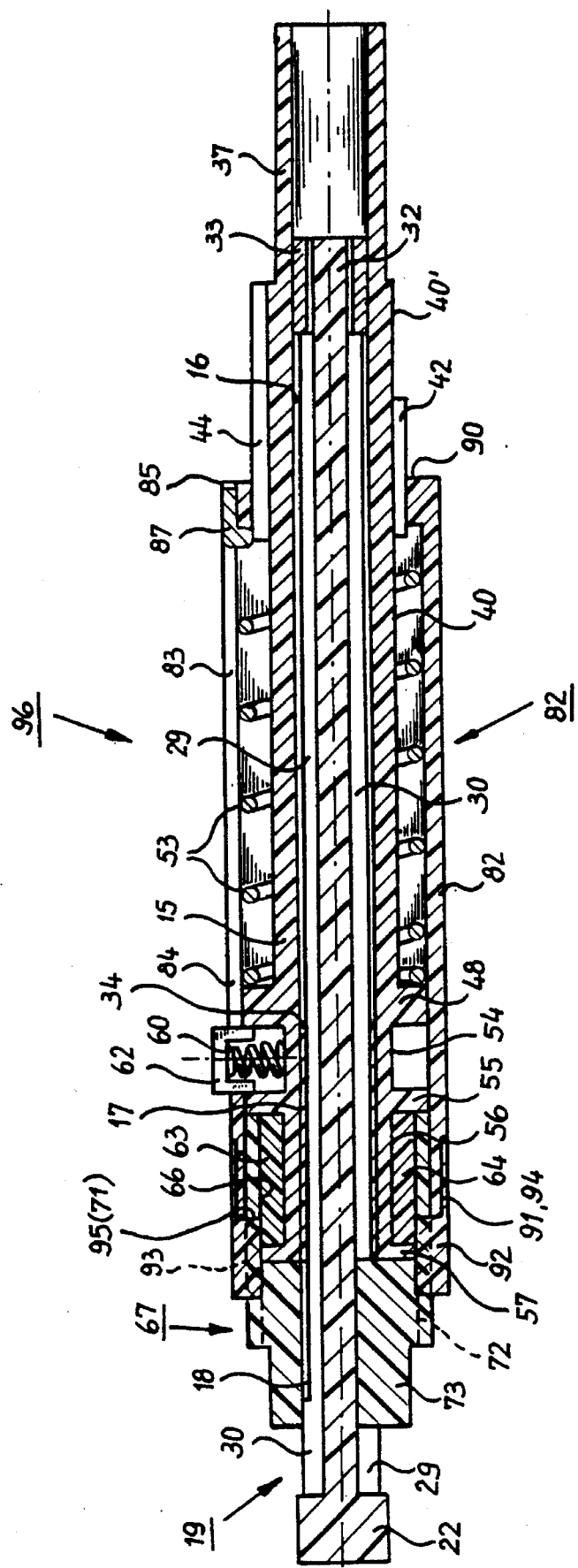
FIG. 5 is a longitudinal section through the assembled element of FIG. 4.

FIG. 1 shows a part 15, which is rotated when the injection dose is set and is therefore called the setting sleeve or positioning sleeve. As FIG. 5 shows, it has a continuous cylindrical recess (through hole) 16, the left end of which is provided with a female thread 17 that serves to receive a male thread 18 of a threaded spindle 19, whose free proximal end 22 may be widened somewhat and serves to act against a plunger 23 (FIG. 17) of the cartridge 11; this plunger is typically made of some suitable rubber and is shown only schematically here.

The female thread 17 and the male thread 18 complementary to it are each preferably a rectangular steep-pitch thread with approximately two thread courses per centimeter, with an outer thread diameter of 0.5 cm. As shown in FIG. 1, the threaded spindle is made in two colors. Its front, proximal part 24 may be white for a length of 1.5 cm, i.e. measured from the proximal end of the threaded spindle 19. The remainder 25 is of a different color, such as red, which is represented by dots in FIG. 1.

As FIG. 17 shows, part B has a window 27 through which the user can check the contents (fill level) of the cartridge 11. When the red part of the threaded spindle 19 becomes fully visible in this window 27, then the user knows it is time to change the cartridge. In FIG. 17, the threaded spindle 19 is not yet visible at all in the window 27, by way of example; in other words, the cartridge 11 is full, but after several injections the plunger 23 moves closer and closer to the proximal end of the cartridge 11, and correspondingly the threaded spindle 19 is screwed more and more out of the adjusting sleeve 15, and then becomes visible in the window 27 (in FIG. 1, the threaded spindle 19 is shown shorter than its actual length; FIG. 5 shows its actual length. FIG. 5 also shows that the male thread 18 of the threaded spindle 19 need not begin until a predetermined distance from the proximal end of the spindle.)

In addition to the male thread 18, the threaded spindle 19 has two diametrically opposed lengthwise grooves 29, 30; see FIGS. 8 and 9, for example. A single lengthwise groove, such the lengthwise groove 29, would intrinsically suffice, but since the threaded spindle 19 is preferably made of plastic, it is more favorable to provide two symmetrical lengthwise grooves 29, 30, since the threaded spindle 19 cannot "warp" or in other words will not become crooked when it is removed from its mold after the plastic injection molding process.

On its distal end, the threaded spindle 19 has a portion 32 of reduced diameter on which a cylindrical sleeve 33 is fastened after assembly, for instance by adhesive bonding or thermal deformation. When it moves against the distal end 34 (FIG. 5) of the female thread 17, this sleeve 33 prevents the threaded spindle 19 from rotating farther out of the adjusting sleeve 15; in other words, it acts as a stop.

If the adjusting sleeve 15 and the threaded spindle 19 are rotated relative to one another, then the complete part thus formed, which can also be called a tappet, becomes shorter or longer depending on the direction of relative rotation. Before each injection, a setting is made as to how much longer this complete part should become during an injection, and this adjusts the injection dose prior to the injection.

On its distal end, the adjusting sleeve 15 has a cylindrical portion 37 of reduced diameter, on which after the assembly an actuation knob 38 (see FIGS. 6 and 7, for instance) is mounted, for instance by means of a screw, a snap connection, or firm adhesive bonding. The cylindrical portion 37 is adjoined proximally by a cylindrical portion 40 of somewhat larger diameter, in whose distal region ratchet teeth 42 are provided, which are shown in section in FIG. 14. In the exemplary embodiment, there are eighteen teeth 42 spaced equally apart; this accordingly makes it possible to set eighteen different injection doses. These teeth occupy approximately 330° of the circumference of the adjusting sleeve 15. In the gap between them, there is a lengthwise groove 43 and a widened stop 44 of rectangular cross section, which extends distally past the ratchet teeth 42 as far as the distal end of the cylindrical portion 40. In other words, to the right of the ratchet teeth 42 in FIG. 1, there is a tooth-free portion 40' of the portion 40, into which the widened stop 44 extends. This is shown quite clearly in FIG. 1.

The teeth 42 themselves are preferably embodied such that looking at the distal end of the actuation knob, they allow a clockwise rotation of this knob 38, but not a counterclockwise rotation. The actuation knob 38 may be provided with a scale 46 for setting the injection dose (see FIG. 6), and a fixed scale marking 47 (see FIG. 6) corresponds on the housing to this scale.

Alternatively, the scale marking may naturally be provided on the actuation knob 38, which serves as an adjusting member, while in that case the scale 46 is then on the stationary housing part 116; this has the advantage that the numbers of the scale 46 can be larger there and as a result can be more legible. This variant is not shown in the drawing.

Figure 3:
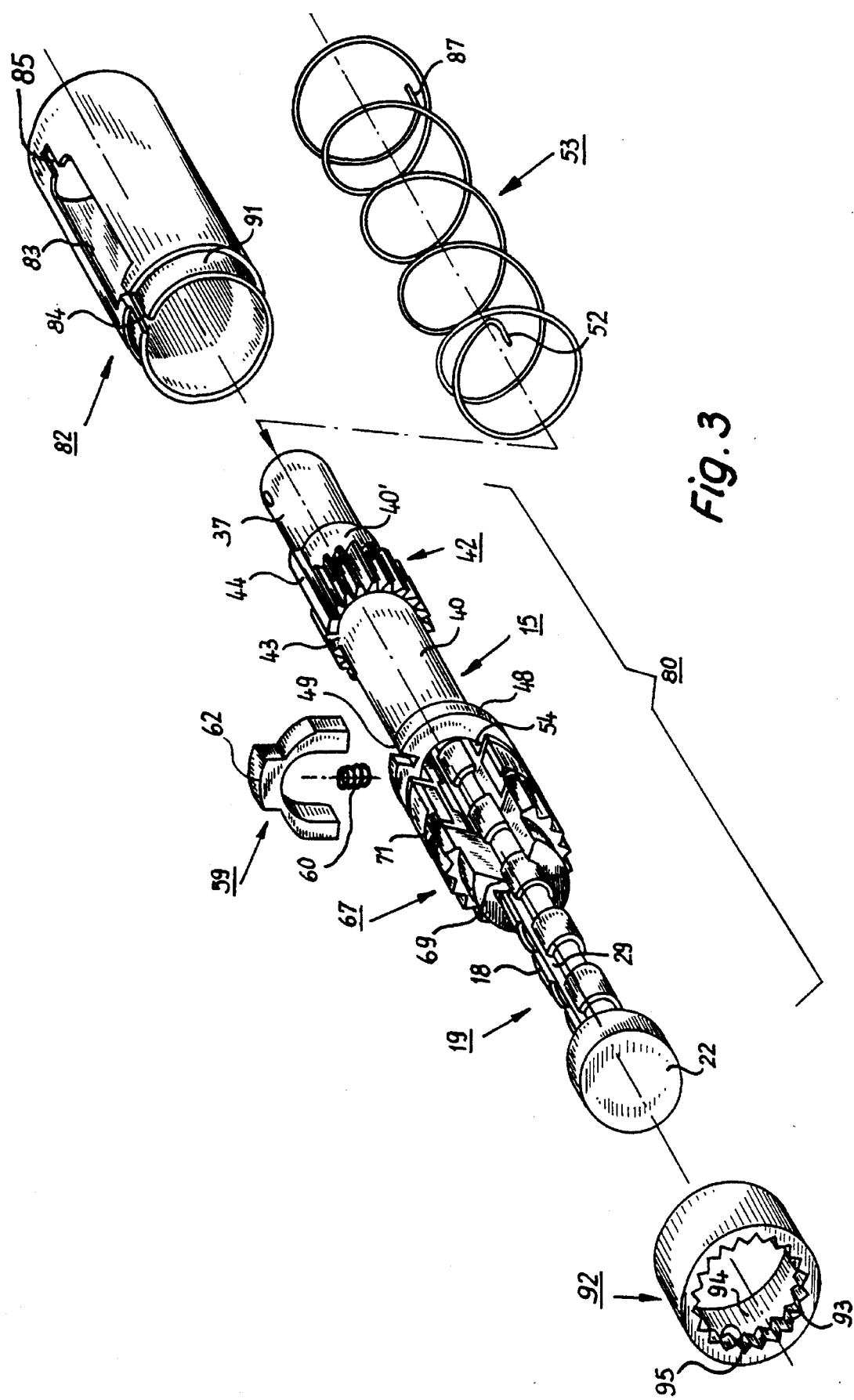
FIG. 3 is a three-dimensional view of the element of FIG. 2 along with further elements of the injection device, prior to their assembly.

At the proximal end of the cylindrical portion 40, this portion changes into a radially protruding flange portion 48, which is provided with a discontinuity for receiving the proximal end 52 of a helical spring 53 (FIG. 3). A flange portion 55 is separated from the flange portion 48 by an annular groove 54, and a flange portion 57 on the proximal end of the adjusting sleeve 15 is separated from the flange portion 55 by an annular groove 56 (FIG. 1). The adjusting sleeve 15 is preferably an injection molded part made from some suitable plastic; see FIGS. 1 and 5.

As FIG. 3 shows, the annular groove 54 serves to receive a detent member 59, which has approximately the shape of an inverted U and is pressed radially outward out of this annular groove 54 by a small spiral spring 60. Its actual detent protrusion is marked 62.

The annular groove 56 (FIG. 1) serves to receive two resilient half shells 63, 64 of plastic, over which a cylindrical internal recess 66 (FIG. 5) of a guide member 67 is slipped when they are located in the annular groove 56. In the process part 67 is preferably adhesively bonded to the half shells 63, 64, so that they firmly hold the guide member 67 on the proximal end of the positioning sleeve 15.

The resilient half shells 63, 64 have a multiple function:

a) They reliably hold the guide member 67 firmly on the proximal end of the adjusting sleeve 15; that is, a force of a dozen newtons (N) or more is needed to pull off the guide member 67.

b) On the other hand, they enable very simple mounting assembly of the guide member 67.

c) They enable rotating the guide member 67 relative to the adjusting sleeve 15; in the context of the invention, this rotation should intentionally not be too easy, because of the action of friction of the resilient half shells 63, 64, and so these half shells 63, 64 can therefore be adapted to brake this rotation to the desired extent. For instance, they may be provided with small protrusions on their inside, which engage corresponding detent teeth (not shown) on the bottom of the annular groove 56, or the like.

Naturally, the guide member 67 could also be secured rotatably on the proximal end of the adjusting sleeve 15 in some other manner; doubtless one skilled in the art will be aware of a great many possibilities for achieving this. However, the version shown is preferred because of its great simplicity.

The guide member 67 has an axial recess 68 (FIG. 1) for the threaded spindle 19, and this axial recess 68 is provided with a guide protrusion 69 projecting radially inward; after assembly it engages the longitudinal groove 29 of the threaded spindle 19, as FIG. 3 shows. Accordingly if the threaded spindle 19 is rotated, for instance by hand, then this also rotates the guide member 67, and if the guide member is restrained against rotation, then the threaded spindle 19 is likewise prevented from rotating, as will readily be appreciated.

This capability of free rotation of the threaded spindle 19 is utilized in order to rotate it manually—after loading a new cartridge 11—all the way back into the adjusting sleeve 15, or in other words even somewhat farther than what is shown in FIG. 5.

To this end, the adjusting sleeve 15 is restrained while the guide member 67 is freely rotatable.

To set the dose, the entire adjusting sleeve 15, guide member 67 and threaded spindle 19 are rotated forward in the same direction, as will be described below; that is, all three parts rotate by the same angle, as desired by the user, such as 30°.

The two ends 52, 87 of the spring 53 are rotated relative to one another, and the spring 53 is cocked for torsion, or its torsional prestressing is increased thereby.

When it is said here that all the parts mentioned are rotated "forward" this means a clockwise rotation in the exemplary embodiment, looking toward the distal end of the injection device 10. Similarly, "backward" means a corresponding counterclockwise rotation.

Next, for injecting the set quantity of fluid, the guide member 67 is restrained from rotation in the housing of the injection device 10 in its proximal end position (FIG. 7), and the adjusting sleeve 15 is rotated backward by the previously set angle, such as the aforementioned 30°, by the torsional force of the spring 53; as a result, the threaded spindle 19 is rotated out of the female thread 17 by a corresponding distance, and in this process it displaces the plunger 23 in the cartridge 11 correspondingly and expels the set dose of fluid from the cartridge.

From the ensuing description, these processes, which in actuality proceed automatically and very quickly, will become still clearer to the reader.

Figure 19:
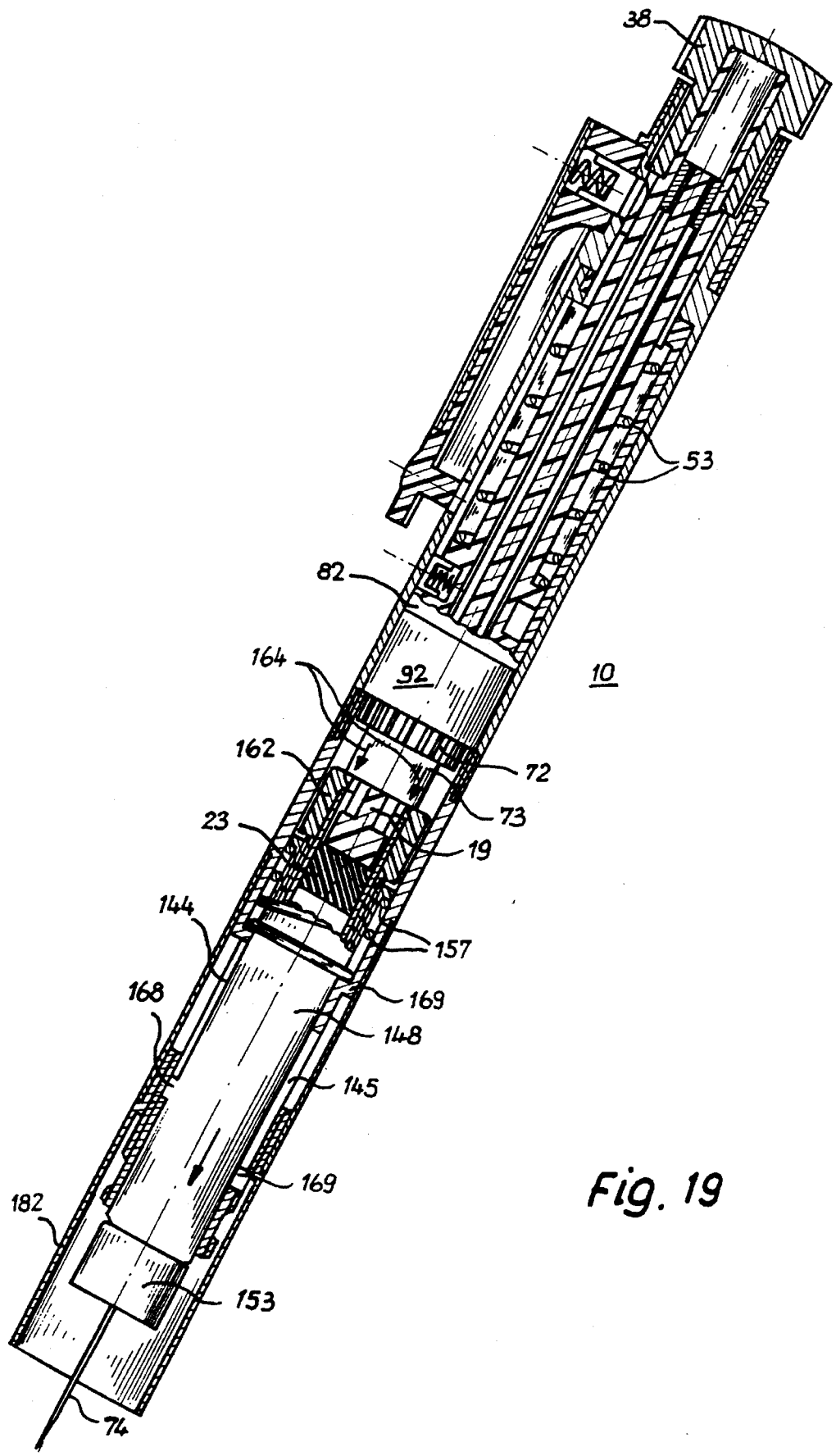
FIG. 19 is a complete view of the injection device of FIGS. 17 and 18 after penetration but before the injection of the fluid.
Figure 20:
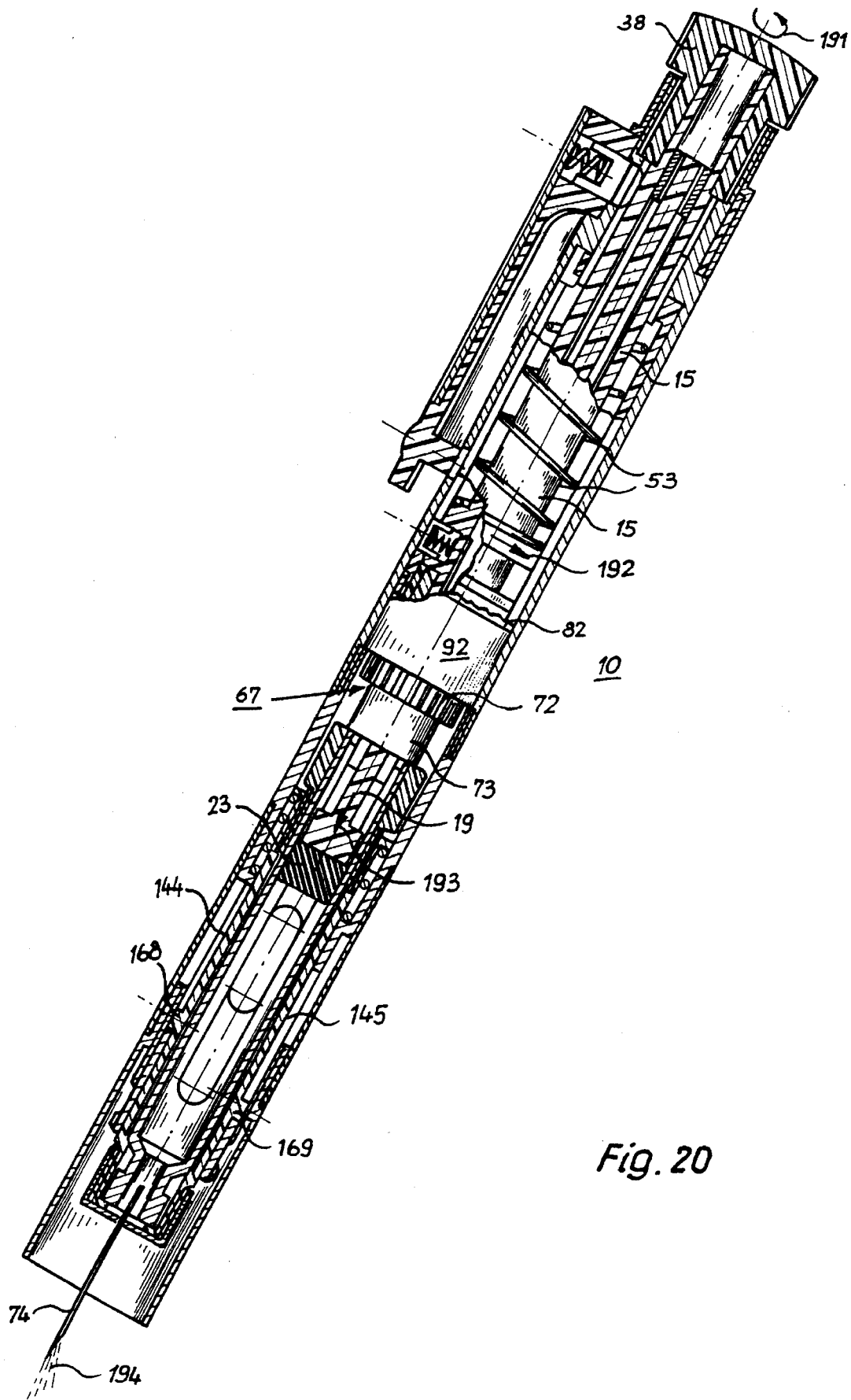
FIG. 20 shows the process of the injection of injection fluid with the injection device of FIGS. 17–19.

The guide member 67 is provided on its outside circumference with a set of axial teeth 72 that extend distally up to a shoulder 71. In practice, the diameter of this set of axial teeth can decrease somewhat proximally; that is, the height of the teeth may decrease by approximately 0.5 to 1% in the proximal direction. In that case, the set of teeth looks very slightly frustoconical. This makes their function easier. The portion 72 having the axial teeth is adjoined by a cylindrical portion 73 of smaller diameter, having the function in the injection process to displace the cartridge 11, and an injection needle 74 secured to it, in the proximal direction and thereby to inject the needle 74 into the patient. This process is shown in FIG. 19. It precedes the injection of the set quantity of fluid, which is shown in FIG. 20.

Figure 2:
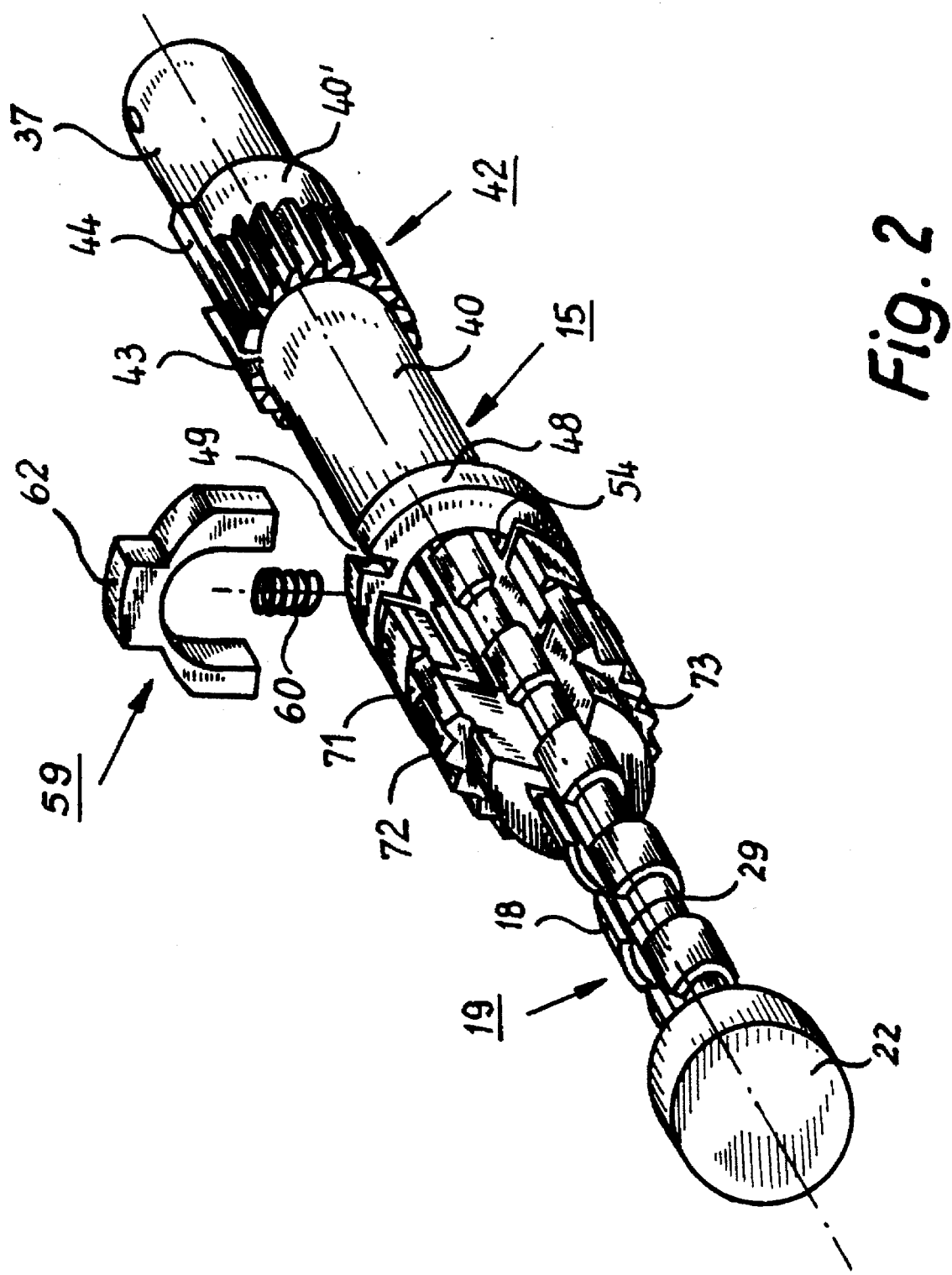
FIG. 2 is a three-dimensional view of the elements of FIG. 1 after their assembly.

When the parts shown in FIG. 1 are assembled, the half shells 63, 64 are first inserted into the annular groove 56; next, internal recess 66 of the guide member 67 is pressed over these half shells 63, 64, so that it assumes the position shown in FIG. 2 and can be rotated on the adjusting sleeve 15 but cannot be displaced relative to that sleeve, because it rests by its distal edge 75 against the proximal side 76 of the flange 55, forming an axial slide bearing together with it (see FIG. 1).

Once the guide member 67 is assembled, the distal end of the threaded spindle 19 is pushed into the opening 68, until that end comes to engage the female thread 17 of the adjusting sleeve 15, and is then screwed into that female thread 17. Next, the cylindrical sleeve 33 (FIG. 5) is secured to the portion 32 of the threaded spindle 19, so that it is no longer possible then for the threaded spindle 19 to be unscrewed all the way out of the female thread 17, and if such an attempt were made, the sleeve 33 acts as a stop.

The assembled part, which as noted may also be called a tappet 80, then has the form shown in FIG. 3.

According to FIG. 3, the detent member 59 already described is then inserted together with the spring 60 into the annular groove 54, and then the spring 53 is pushed over the distal end of this tappet 80; the proximal end 52 of the spring 53 engages the recess 49 and consequently can transmit a torque from the spring 53 to the adjusting sleeve 15, and can also transmit an axial force if the spring 53 is correspondingly cocked.

It is appropriate to point out here that the spring 53 in the exemplary embodiment serves not only to generate an axial force upon the adjusting sleeve 15 but also to generate a torque, with the goal of rotating this adjusting sleeve.

Once the spring 53 has been mounted, a sleeve 82 of plastic is pushed over the adjusting sleeve 15 from the distal end. This sleeve 82 has a relatively wide axial lengthwise groove 83 in its middle region, which on the proximal end continues as a narrow lengthwise groove 84 and on the distal end continues as a narrow lengthwise groove 85.

Figure 4:
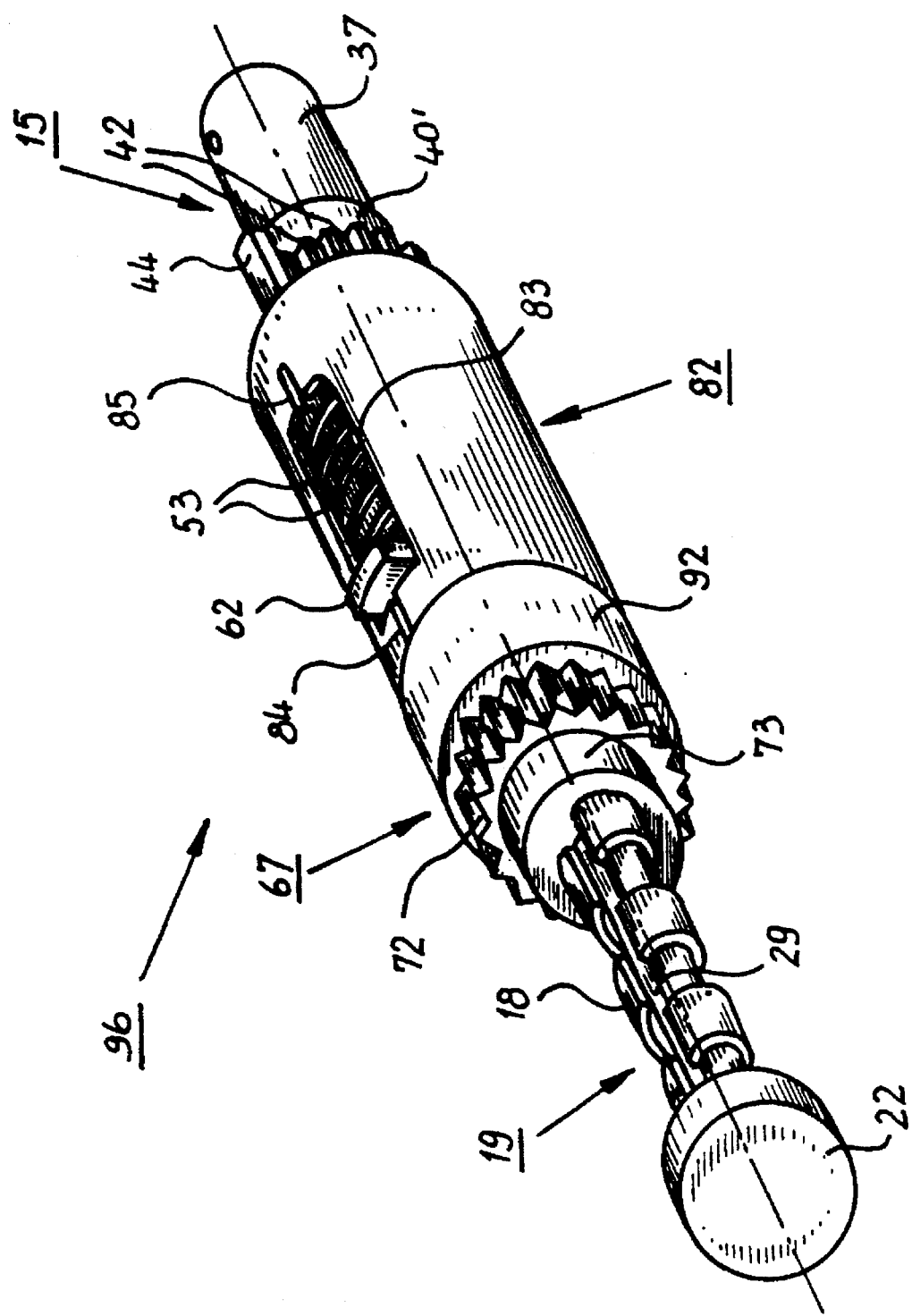
FIG. 4 is a three-dimensional view of the elements of FIG. 3 after their assembly.

The wide lengthwise groove 83 serves to receive the detent tang 62 of the detent member 59; in other words, as shown in FIG. 4, this detent tang 62 protrudes out of the wide longitudinal groove 83 and can be pressed radially inward counter to the action of its spring 60.

The distal end 87 of the spring 53 protrudes into the narrow lengthwise groove 85 of the sleeve 82, where it is secured against both rotation and axial displacement. This is also shown quite clearly in FIG. 5.

On its distal end, the sleeve 82 has a radially inwardly protruding flange 90, with which it can slide on the ratchet teeth 44; see FIG. 5. This flange 90 serves as a detent for the distal part of the spring 53. On its proximal end, the sleeve 82 has a portion 91 of reduced diameter.

A sleevelike part 92 is pushed onto the portion 91 from the proximal end; it is provided with internal teeth 93, complementary to the external teeth 72, in its proximal region, while in its distal region it has a cylindrical internal recess 94 which corresponds approximately to the outside diameter of the portion 91 and can be pushed onto it—preferably only in one predetermined rotational position which is defined by the engagement of a protrusion (not visible) of the part 92 with the narrow lengthwise groove 84; some adhesive is placed between the portions 91 and 94, and as a result these portions are adhesively bonded to one another. The axial force of the tenshioned spring 53 in this case presses the guide member 67 with its external teeth 72 into the internal teeth 93 of the sleevelike part 92, and as shown in FIGS. 4 and 5, the guide member 67 protrudes with its external teeth 72 out of this set of internal teeth 93 to some extent.

A shoulder 95 (FIG. 5) on the distal end of the inner teeth 93 acts during the injection as an axial stop for the shoulder 71 (FIG. 1) on the distal end of the external teeth 72 and thus precisely defines the proximal end position of the guide member 67 relative to part 92.

These assembly procedures accordingly produce the part 96 as shown in FIGS. 4 and 5. If in FIG. 4 the sleeve 82 of the part 96 is firmly held and the adjusting sleeve 15 is rotated at its portion 37, then the threaded spindle 19 is rotated either out of or into the adjusting sleeve 15, depending on the direction of rotation. In this process the detent member 59 turns in the annular groove 54, while the guide member 67 is secured against rotation relative to the sleeve 92 by the internal teeth 93.

It should be pointed out here that the guide member 67, in its proximal end position, must a) assume a predetermined axial position relative to the housing, and b) be blocked against rotation.

To achieve these goals, there are naturally many options. For instance, it would also be possible for the guide member 67 in its proximal end position to simply rest with a proximal shoulder analogous to the shoulder 71) against a corresponding distal shoulder of the part 92 (analogous to the shoulder 95) with sufficient friction, or for suitable protrusions and indentations complementary to them to be provided on these shoulders, which securely prevent rotation of the guide member 67 relative to the part 92 in this position. This option is not shown separately in the drawing.

The part 96, in its form shown in FIGS. 4 and 5, is now ready for being mounted in the housing of the injection device 10. As FIG. 6 shows, this housing has a part in the form of a tube 100, for instance of aluminum, with a cylindrical recess 102 that is adapted to the outside diameter of the part 96 and can receive it without play. An annular shoulder 103 in the distal part of the tube 100 acts during assembly as a stop for the distal end of sleeve 82 (see FIG. 7).

Figure 10:
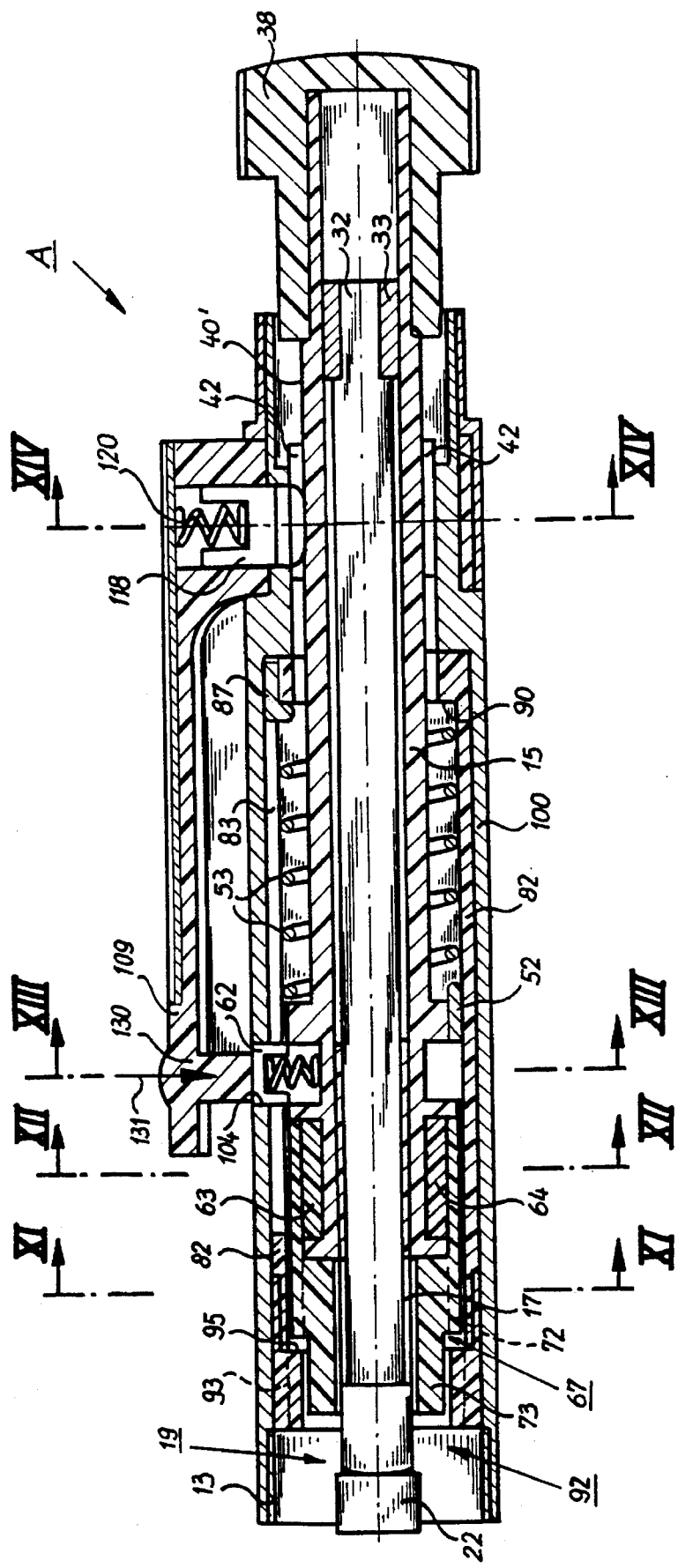
FIG. 10 is a longitudinal section through the element of FIG. 7 in the cocked state and after an injection dose has been set; this is the same position shown in FIG. 18.

Part 96 is inserted into the cylindrical recess 102 of the tube 100 in such a way that a rectangular lateral opening 104 of tube 100 is aligned with the widened lengthwise groove 83. Thus if the adjusting sleeve 15 is displaced distally by being pulled, in the course of which the spring 53 is cocked, then the detent tang 62 can lock into place in this opening 104, as shown in FIGS. 10, 13 and 18. This is the cocked position of the injection device 10, in which it must be put before an injection so that a dose can even be set at all. In this position, the spring 53 is cocked and as a result stores the energy necessary for inserting the needle 74 into the patient.

Accordingly, the part 96 is inserted into the tube 100 in this position, and in this position the sleeve 82 is permanently secured in the tube 100, for instance by adhesive bonding, with a screw, or in some other suitable way.

The tube 100 has an outer cylindrical portion 103 of reduced diameter on its distal end, and in its interior it has a cylindrical portion 104 of reduced diameter, which extends away from the shoulder 103 in the distal direction up to a shoulder 105, where this portion 104 changes into a cylindrical portion 106 of somewhat larger diameter, which extends up to the distal end of the tube 100 (FIG. 7).

Once the part 96 has been assembled, a clip 108, which has a resilient clip portion 109 and an annular portion 110, is slipped onto the cylindrical portion 103, which is provided with a narrow radial recess 107. A cylindrical hole 113 of portion 110 fits without play over the cylindrical portion 103. The clip 108 has a radially extending recess 114, which in the assembled state is aligned with the radial recess 107 of the tube 100. In this aligned position, the annular portion 110 is secured to the cylindrical portion 103, for instance by adhesive bonding. Alternatively, it can be press-fitted onto this portion.

Next, a tubular cover ring 116, which has a rectangular recess 117 for the clip segment 109, is slipped over the cylindrical portion 103 of tube 100 and the outside of the annular portion 110 and secured in that position, for instance by adhesive bonding. The specific shape of this cover ring 116 is shown in FIG. 7, for instance.

Once the cover ring 116 has been secured, the rotatable knob 38 can be secured to the portion 37 of the setting sleeve 15, as has already been described.

For engagement with the ratchet teeth 42 or with the stop 44, a pawl 118 is provided, the cross-sectional shape of which is clearly shown in FIGS. 7 and 9. It should be pointed out once again that the views of FIGS. 8 and 9 are on a larger scale than FIG. 7, for better comprehension of the invention.

The pawl 118 is simply inserted from above into the recesses 114, 107, but not until after the knob 38 has been rotated clockwise (as viewed from the distal side of the injection device 10) by a predetermined angle, far enough that the spring 53 has been cocked to a predetermined torque. Typically, a half revolution of the knob 38 suffices for this. In this cocked position, the pawl 118 is dropped into the recesses 114, 107—in the manner of a guillotine—so that it comes to rest with its inner end on the portion 40' of the cylindrical portion 40 (FIGS. 7 and 9).

The knob 38 can now be let loose, and because of the prestressing of the spring 53, the protrusion or stop 44 presses against this pawl 118, as FIG. 9 shows.

Above the pawl 118, a small helical spring 120 is mounted, and above that a cover plate 122 is thrust into two grooves 124, 124', parallel to one another, of the clip 109 and thus effects a corresponding prestressing of the spring 120 (FIG. 9).

Part A of the injection device 10 is now completely assembled and ready for use. It is a miracle of mechanics, because it makes for extraordinarily simple use.

Mode of Operation of Part A

FIG. 7 shows part A in the basic position, and FIG. 10 shows it in its cocked position after an injection dose has been set.

What happens if an attempt is made to set an injection dose in the basic position of FIG. 7?

In that case, the external teeth 72 of the guide member 67 are in engagement with the internal teeth 93, or in other words with the housing of the injection device. Consequently the guide member 67 cannot rotate in this position.

The stop 44 (see FIG. 9, for example) enables only clockwise rotation of the actuation knob 38, viewed from the distal end of the injection device 10. The consequence of such a rotation is that the threaded spindle 19 is screwed into the adjusting sleeve 15; that is, the tappet 80, shown in FIG. 3 becomes shorter, not longer. Upon such a rotation of the actuation knob 38, the spring 53 is additionally cocked for torsion. If the actuation knob 38 is let go, then the spring 53 rotates the actuation knob 38 back into its initial position in which the stop 44 rests against the pawl 118, as FIG. 9 shows, and the threaded spindle 19 likewise resumes its previous position.

Accordingly, it is demonstrated that an attempt to set a dose in the basic position (FIG. 7) will be fruitless, and in this process the tappet 80 (FIG. 3) becomes not longer but shorter. As a result, it is possible to build an injection device that is quite short, because in the basic position increasing the length of the tappet 80 (FIG. 3) is impossible, and consequently no additions for safety purposes need to be provided.

Once part A is cocked, as shown in FIG. 10, the detent tang 62 locks into place in the recess 104 of the tube 100, and by this cocking procedure the spring 53 becomes more strongly biased.

As FIG. 10 clearly shows, the outer teeth 72 of the guide member 67 become disengaged from the inner teeth 93 of part 92 in this position, so that the guide member 67 can now rotate freely and unhindered in the interior of the sleeve 82. This kind of friction-free and unhindered rotation is necessary for correct setting of the injection dose, so that during the setting procedure a relative rotation between the adjusting sleeve 15 and the guide member 67 is reliably avoided. For that reason, it is also advantageous if, as described at the outset, a certain minimum torque is needed to enable such a relative rotation.

In the position shown in FIG. 10, the pawl 118 engages the portion having the detent teeth 42 whose shape can be seen in FIG. 14 and has already been described. Upon the rotation, the pawl 118 snaps behind each tooth 42 and in so doing makes a clicking noise which can be counted by the user and thus gives him/her acoustical information on the dose set, if he/she is blind or visually impaired. FIG. 14, purely by example, shows a rotation by 54° in the direction of the arrow 128, corresponding to three detent teeth 42. (In the exemplary embodiment, ten detent teeth 42 per 180° are provided; that is, the angular spacing α between two detent teeth 42 is 18° in the exemplary embodiment.)

Not only the adjusting sleeve 15 but also the guide member 67, which moves freely in this position, and the threaded spindle 19 are rotated by precisely these 54° rotations; in other words, absolutely nothing in the total length of the tappet 80 (FIG. 3) changes as a result of this adjusting process. The tappet 80 did not become any longer. How could anything be injected in that case?

The resilient clip segment 109 now serves to trip the injection procedure; it is provided with an inwardly projecting protrusion 130 that faces the opening 104 and can plunge into it if pressure is exerted by a finger upon this clip segment 109 in the direction of the arrow 131 (FIG. 10).

This presses the detent tang 62 inward, and this tang 62 now no longer restrains the tappet 80 (FIG. 3) in its cocked position, so that the tappet is displaced proximally by the cocked spring 53. As will be seen below, this displacement causes the injection needle 74 to puncture the flesh of the patient, as FIG. 19 indicates.

This displacement now causes the guide member 67 to slide with its external teeth 72 into the internal teeth 93. A glance at FIG. 11 illustrates that these teeth have the same tooth pitch (18° in the exemplary embodiment) as the detent teeth 42, so that in any of the possible detent positions of the adjusting sleeve 15, the external teeth 72 can slide easily and without difficulty into the inner teeth 93. (As described, the part 92 is secured in a suitable, predetermined rotational position on the sleeve 82.)

Accordingly, while the outer teeth 72 slide smoothly into the inner teeth 93, thereby reliably preventing the guide member 67 from making any rotation relative to the housing (tube 100 of part A), the pawl 118 slides out of the region having the detent teeth 42 and into the region 40' of the adjusting sleeve 15. This produces an overlap; that is, not until the outer teeth 72 engage the inner teeth 93 does the pawl 118 slide all the way out of the detent teeth 42.

Once the pawl 118 has left the detent teeth 42 completely, it can no longer prevent rotation of the adjusting sleeve 15 by the torsionally cocked spring 53, and this spring 53 then rotates the adjusting sleeve 15 back again by the previously set angle; that is, looking at the distal end of the actuation knob 38, this knob, once it has again reached the position of FIG. 7, is rotated counterclockwise back again by the angle previously set (when the dose was set). In the example of FIG. 14 with three detent teeth 42 occupying an angle of 54°, the adjusting sleeve 15 is accordingly rotated back counterclockwise by 54°. Since the guide member 67 is nonrotatable relative to the housing (tube 100) in this process, it is this rotation of the adjusting sleeve 15 that first brings about screwing out of the threaded spindle 19 from the female thread 17 of the adjusting sleeve 15, and thus effects the injection of the set dose.

The following advantages will now be appreciated:
a) Until just before the end of the injection procedure, the tappet 80 (FIG. 3) maintains its earlier length, and only toward the end of the injection procedure does it become longer. As will readily be seen, this makes a very short structural length of the injection device possible.
b) The injection of the set dose does not take place until the needle has already punctured the flesh of the patient.
c) Even if there is some air in the cartridge 11, no injection fluid is lost. Air in the cartridge 11 in fact acts like a spring there and retards the injection procedure. The patient need merely keep the needle 74 in the inserted condition until the injection procedure has been concluded. He will be taught this in the course of being trained for this injection device.
d) After the injection, the injection device 10 is in its Zero position; that is, the value "zero" on the scale 46 (FIG. 6) again automatically faces the housing marking 47, which is located on the cover ring 116, without the patient having to do anything to achieve this.
e) Consequently, an injection is reduced to the following simple steps:
cock
set dose
place injection device against flesh
actuate When used in veterinary medicine, this saves a great deal of time, and when used in human medicine, incorrect use is virtually precluded, because the patient can actually no longer do anything wrong. At best, he might forget to set his injection Dose, but in that case nothing whatever will be injected. It is inevitable that that should be so, because the injection device Can after all not "guess" the dose that the patient needs at that instant, and which often he will have determined himself shortly beforehand. Optionally, however, tripping of the injection device 10 may be blocked in the position "zero" as described in European Patent 0 349 592 B1, for instance, which will remind the patient that he has to set the injection dose before tripping the injection.

The option of tripping an injection in the "zero" dose position as well has the advantage that the device can be used for drawing blood, if a special needle is used, of the kind shown and described in German Patent Disclosure 38 42 317 A1. In this needle, a sterile covering for the needle is used as in the typical case, but this covering has a small lancet on its proximal end for drawing blood. In the "zero" dose position, the device according to the invention can now be used to insert this lancet into the patient painlessly. This is possible because at the "zero" dose setting, the device does not expel any injection fluid, and the needle 74 or in this case the lancet is driven by the part 73 of the guide member 67, not by the threaded spindle 19 as in the aforementioned European Patent 0 349 592 B1. This "direct drive" of the needle, as will be described in detail below, proves in practice to be quite advantageous and also therefore provides greater safety, because it precludes the possibility of the patient injecting injection fluid whenever the device is set to the "zero" dose.

Figure 15:
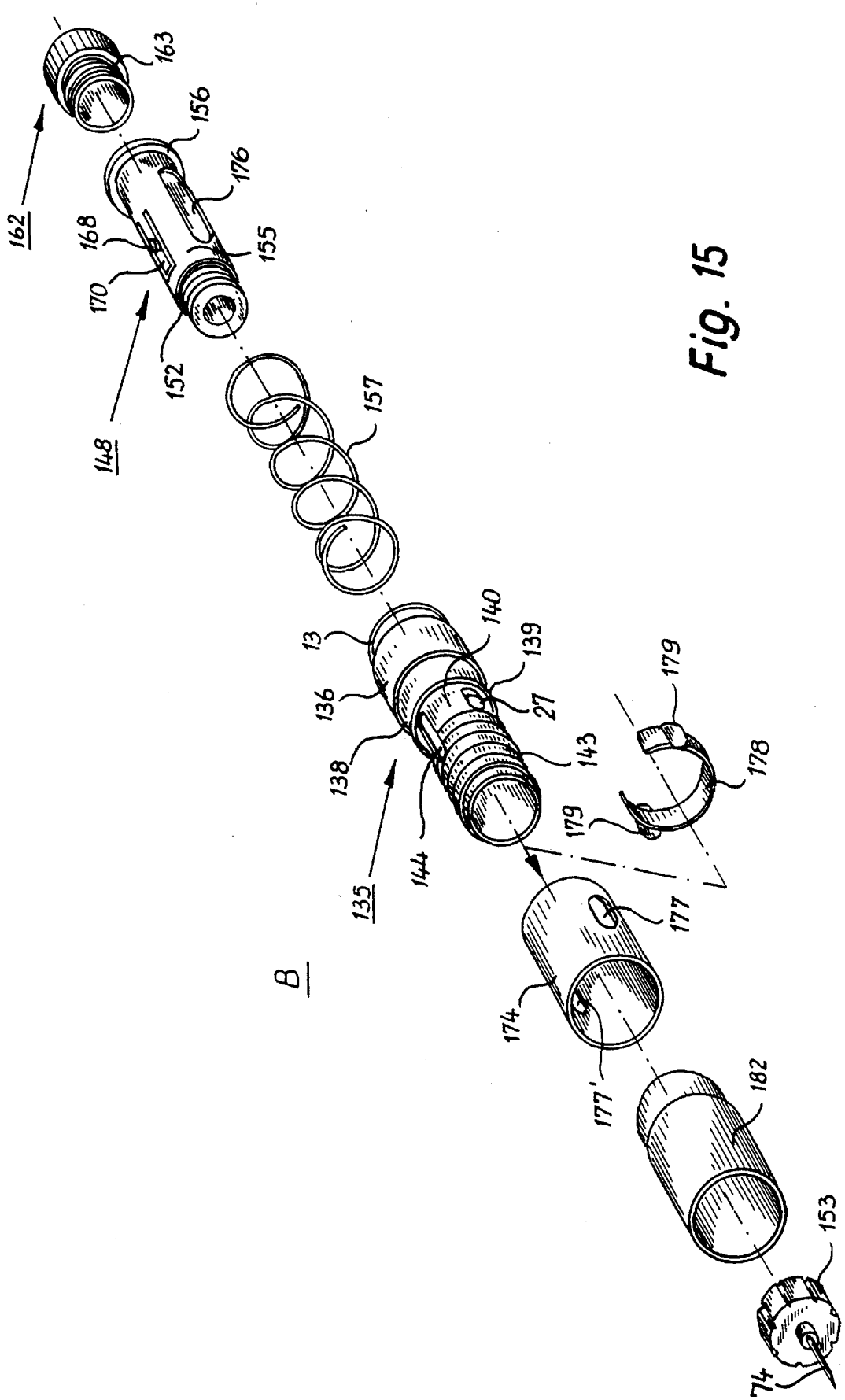
FIG. 15 is a three-dimensional view of the part of the injection device that serves to receive a cartridge (not shown in FIG. 15) holding the fluid to be injected.

Part B (FIGS. 15 and 16)

FIG. 15 shows the various individual parts of part B, and FIG. 16 shows part B in the assembled state, in longitudinal section.

For connection to part A, the male thread 13 on a tubular part 135 is used; this latter part may be made of aluminum, for instance. Beginning at the male thread 13, the part 135 has first a cylindrical portion 136, which preferably has the same diameter as the tube 100. Via a shoulder 137, the portion 136 changes into a cylindrical portion 138 of somewhat smaller diameter, which in turn changes via a shoulder 139 into a portion 140 of smaller diameter whose proximal region is provided with a male thread 143.

The portion 140 has two oblong slots 144, 145, facing one another, which in the embodiment shown are axially offset from one another somewhat for production reasons; that is, the oblong slot 145 is closer to the proximal end of the tubular part than the oblong slot 144, as is clearly shown in FIG. 16.

The portion 140 also has two diametrically opposed viewing windows 27, which have already been described and are used to observe the fill level of the cartridge 11. (This is not shown in FIG. 15.) The cylindrical internal recess of portion 140 is marked 141 (FIG. 16).

A cartridge holder 148 is shaped for being received in the tubular part 135 and in turn, as shown in FIG. 16, serves to receive a cartridge 11. It is typically made of metal, such as aluminum, but may also be made of some sturdy plastic.

The cartridge holder 148, which is displaceable in the tubular part 135, tapers on its proximal end and there forms a flange 149 that projects radially inward and against which the proximal end 150 of an inserted cartridge 11 rests. The proximal end of the cartridge holder 148 is provided with a male thread 152 onto which a sleeve 153 in which the needle 174 is secured can be screwed. In the usual way, the cartridge 11 has a thin rubber membrane (not shown) on its proximal end; this membrane is pierced by the distal end of the needle 74. The needle 4 can thus easily be replaced after an injection, as is well known to one skilled in the art.

The cartridge holder 148 also has a substantially cylindrical outer portion 155 which distally adjoins the outer thread 152 and extends up to an annular shoulder 156 at the distal end of the cartridge holder 148; this annular shoulder 156 serves as an abutment for a helical spring 157, which in the mounted state is disposed around the cartridge holder 148, and whose other end in the mounted state rests against the distal end of annular shoulder 139.

The cylindrical internal recess of cartridge holder 148 marked 158. On its distal end, it is provided with a female thread 160, into which in the mounted state, a screw 162, knurled on the outside, is screwed with a corresponding male thread 163; this firmly holds the cartridge 11 in the inner recess 158, as FIG. 16 shows. The knurled screw 162 has a central opening 161, which has approximately the same diameter as the interior of the cartridge 11. Through this opening 161, the threaded spindle 19 can pass unhindered, as shown in FIG. 16. On the other hand, as FIG. 19 shows, for example, the screw 162 is designed such that at the beginning of an injection, when the spring 53 moves the portion 73 of the guide member 67 in the proximal direction, this portion 73 rests against the distal end of the screw 162 and displaces it proximally, as indicated by the arrows 164 of FIG. 19, counter to the action of the spring 157, causing the needle 74 to pierce the flesh of the patient, in fact before the threaded spindle 19 becomes operative and expels the previously set quantity of fluid from the cartridge 11.

Accordingly, the spring 157 is slipped over the cartridge holder 148, which is then slipped into the cylindrical inner recess 141 of the tubular part 135.

The cartridge holder 148, on its outside, has two radially outwardly projecting protrusions 168, 169, each disposed on one resilient tongue 170 and 171, respectively. These protrusions 168, 169 are offset from one another by the same amount as the two oblong slots 144, 145, and upon assembly they are pressed inward somewhat, and then after assembly each snaps into "its own" oblong slot—that is, protrusion 168 snaps into the oblong hole 144 and protrusion 169 snaps into the oblong hole 145. They thus limit the axial displacement of the cartridge holder 148 in the tubular part 135 in both directions.

As the needle 74 pierces the flesh of the patient, the protrusions 168, 169 are displaced as far as the proximal end of the associated oblong holes 144 and 145, and as a result they limit the depth to which the needle 74 penetrates. When a new cartridge 11 is inserted, they limit the motion of the cartridge holder 148 in the distal direction or in other words out of the tubular part 135; it is then readily possible for the knurled part of the screw 162 to be grasped with the fingers and unscrewed, for instance to remove the cartridge 11 or insert a new one. (This position of the cartridge holder 148 is not shown in FIG. 16).

The cartridge holder 148 has two observation holes 175 (FIG. 16) and 176 (FIG. 15) in the form of oblong holes, which face the observation openings 27 of the tubular part 135 and make it possible to monitor the fill status of the cartridge 11 continuously, along with the position of the threaded spindle 19, as described at the outset. Since upon use, the cartridge holder 148 is displaced in the part 135, its observation holes 175, 176 must be longer than the observation openings 27, as will readily be appreciated.

After the insertion of the cartridge holder 148 into the tubular part 135, a tube section 174 can now be mounted; it is likewise provided with two observation holes 177, 177' (FIG. 15), which are diametrically opposite one another. These observation holes 177, 177' are closed off from the inside by a clip 178 of transparent plastic which carries two small disks 179 (FIG. 15) that after assembly fit precisely into the observation holes 177, 177' and close them off in a dustproof manner, so that no foreign matter or dirt can get into the injection device 10 and impede its function. The tube section 174 provided with the clip 178 is slipped over the cylindrical segment 138 of the tubular part 135 and secured there, for instance by adhesive bonding. It has the same outside diameter as the tube 100.

Next, a tube 182 for adjusting the depth of penetration into the flesh is screwed onto the male thread 143 of the tubular part 135 by means of a female thread 183 with which it is provided on its distal end; the tube 182 may be made of aluminum, for example. The female thread 183 is located on a portion 184 of reduced diameter of the tube 182, and this portion 184 is screwed under the proximal end of the tube section 174 upon assembly. By rotating the tube 182, the depth to which the needle 74 penetrates can be changed by the user; that is, if the tube 182 is screwed outward in the proximal direction, the needle 74 penetrates less deeply.

Mode of Operation of the Injection Device 10

To load a new cartridge 11, part A and part B are unscrewed from one another at the screw connection 13. The knurled screw 162 is unscrewed from the cartridge holder 148, the old cartridge is removed and a new cartridge 11 is inserted, and the knurled screw 162 is screwed in again.

Part A and part B remain separate initially, and part A is now put in the cocked position shown in FIG. 10; in this position, the threaded spindle 19, by being turned manually, is screwed all the way back into the adjusting sleeve 15, or in other words even farther than what is shown in FIG. 10. Next, part A is tripped by pressure upon the slip 109, whereupon it assumes the position shown in FIG. 7.

Part A and part B can now be screwed together again (by means of the threads 13), resulting in the situation shown in FIG. 17; that is, the injection device is in its basic position.

In this position, part 73 of the guide member 67 presses against the knurled screw 162 and as a result compresses the spring 157 somewhat. The user now suitably makes a test injection; that is, he puts the injection device 10 into the cocked position of FIG. 18, and as a result the knurled screw 162 is now put into contact with part 92 of part A, by means of the spring 157.

After the injection device is cocked, the user rotates the actuation knob 38 to set a dose. In FIG. 18, this has already been done and is therefore indicated by a rotary arrow 190 shown in dashed lines. This process of dose setting has already been described above in detail in conjunction with describing the mode of operation of part A.

In FIG. 19, the injection device is then tripped; this causes part 73 of guide member 67 to move proximally and press against the knurled screw 162, which is indicated in FIG. 19 by the arrows 167. This too has already been described in detail above. The spring 157, which is weaker than the spring 53, is compressed in the process, and the needle 74 starts to protrude from the sleeve 182. In this test, the needle 74 is suitably held so that it points upward, so that in this process any air bubbles that may be present will be reliably removed from the cartridge 11.

It has been found that the ratio of the forces of the springs 53 and 157 is important for an optimal course of this process; specifically, the spring 157 must not be too weak. Since in fact the spring 53 also has the function of generating torque, it must be designed primarily for that purpose, and is therefore quite strong—with respect to its capability of generating an axial force. The spring 157 must therefore act counter to it, to prevent the process of penetration of the needle 74 from proceeding too fast, which could cause hematomas, and also in order that cocking the injection device 10 will not become too difficult, especially for elderly patients. In this sense, the difference in forces of the two springs—which after all act counter to one another in the cocking process—plays an important role.

In a practical embodiment, the spring 53 in the cocked state, in other words with the length as shown in FIG. 10, has a force of 18N, and the spring 157 in the cocked state, in other words with the length as in FIG. 17, has a force of 6N; in other words the ratio of forces—in the compressed state in each case—is 3:1. is 3:1. Specific values can be determined in an individual case only empirically, since both springs, on both their outside and their inside, rub on parts of the injection device, and these friction factors cannot be quantified and must be ascertained empirically, in other words by trial and error. The values of 6 N and 18N, which should be understood as suggestions of orders of magnitude, refer to springs that—without friction—are compressed in a measuring instrument to suitable lengths and measured there. After they are installed in the injection device, the measured values are lower because of the friction. Within the scope of the invention, it is naturally not precluded that the dual function of the spring 53, that is, to generate an axial force for the penetration of the needle and to generate a torque for the process of injecting the quantity of fluid to be injected, may be distributed to two different springs, each of which then has only a single function. However, the embodiment shown has the advantage of greater simplicity, since only a single spring 53 is needed for both functions.

If in the test injection the needle 74 is in its injection position, as shown in FIG. 19, in which it would normally be introduced into the flesh of the patient, then the actual process of expelling fluid (and possibly air) from the cartridge 11 takes place as shown in FIG. 20. This process as well has already been described above in detail in the description of the mode of operation of part A. The actuation knob 38, and with it the adjusting sleeve 15, rotates in the direction of the arrows 191, 192 of FIG. 20, while the outer teeth 72 of the guide member 67 are restrained from rotating in part 92. As a result, the threaded spindle 19 moves proximally in the direction of the arrow 193 and displaces the plunger 23 proximally in the cartridge 11, which in-turn can no longer be displaced proximally in the housing of the injection device 10 because the protrusions 168, 169 of the cartridge holder 148 are already in contact with the proximal ends of the oblong holes 144, 145. As a result, a quantity of injection fluid 194 in accordance with the previously set dose is ejected from the needle 74. The user sees this and knows that the injection device 10 is now ready for use and that any air has been removed from it.

The user can then perform the same course of events again, as shown in FIGS. 17–20, and in so doing inject the necessary dose into himself.

An extraordinarily high number of modifications and changes are intrinsically possible within the scope of the present invention, as will be readily apparent to one skilled in the art. For instance, the housing parts could be made of some suitable plastic instead of aluminum, while conversely, parts under heavy strain in the interior of the injection device 10 may be made of metal. In many cases, for instance, it will be practical to select a somewhat smaller diameter for the part 75 than for the shoulder 48, so that there will be no danger that the part 75 will scrape anywhere in the course of setting the dose. The injection device according to the invention, taken as a whole, offers extraordinarily many advantages, especially for so-called intensive insulin therapy, since from a single cartridge 11, containing 100 IU of insulin, for instance, a user can give 20 or more injections as needed before a new cartridge has to be inserted, and the course of the injections is extraordinarily simple and foolproof, as described. It goes without saying that the injection device of the invention is suitable not only for insulin but for any other fluids that must be injected, such as vitamin B12 in the treatment of anemia.

We claim:

1. For combination with a liquid-containing cartridge (11), wherein the cartridge has a plunger (23) displaceably located therein, an injection device for injecting a selected dose of a fluid from the cartridge into a subject, when the injection device is located proximally with respect to the subject, wherein the injection device comprises a housing (100) dimensioned to receive the cartridge (11);

an adjustable-length tappet (80) which is axially displaceable relative to said housing (100) between a proximal end position and a distal end position thereof, including a dose-adjusting member (15) located within the housing (100) and having a thread (17), and a threaded spindle (19) guided in the thread (17) of said dose-adjusting member (15), said threaded spindle (19) being axially aligned with said plunger (23) in said cartridge (11) for acting on said plunger when the cartridge is positioned in the injection device;

a spring means (53) having two ends, which ends are coupled, respectively, to said housing (100) and to said tappet (80) for axially biassing said dose-adjusting member (15) in a proximal direction;

a guide member (67) located in the housing (100), axially slidably located on said threaded spindle (19), and secured against rotation relative to said threaded spindle (19);

rotation-disabling means (92, 93) for disabling rotation of said guide member (67) relative to said housing (100) when said tappet (80) is in the proximal end position thereof while permitting rotation of the guide member (67) in the distal end position of said guide member (67); and retaining means (42, 118) for retaining said dose-adjusting member (15) in a rotational position, selected by a user when setting the dose to be injected by rotating said dose-adjusting member (15) in a setting direction (190), and wherein said retaining means (42, 118) is enabled when said tappet (80) is in its distal end position, and is disabled when said tappet (80) is in its proximal end position.

2. The injection device of claim 1, wherein the spring means comprises a spring (53) located between said housing (100) and said dose-adjusting member (15), the biassing force of said spring being variable by rotation of said dose-adjusting member (15); and wherein said retaining means (42, 118), when in the distal end position of said dose-adjusting member (15), permits rotation of said dose-adjusting member (15) relative to said housing (100) only in a predetermined rotational direction and blocks such rotation in the opposite rotational direction.

3. The injection device of claim 2, wherein said dose-adjusting member (15), when in the distal end position, is adjustable by rotation of said dose-adjusting member in a dose-setting direction, beginning at a predetermined rotary position, wherein said predetermined rotary position acts as a stop at the proximal end position of said dose-adjusting member (15) to limit rotation thereof counter to said dose-setting direction.

4. The injection device of claim 2, wherein said retaining means (42, 118) comprises a pawl (118) and ratchet teeth (42), both disposed between said dose-adjusting member (15) and said housing, said pawl (118) engaging said ratchet teeth in the distal end portion of the tappet (80).

5. The injection device of claim 2, wherein said retaining means (42, 118) forms a block with respect to rotation of said dose-adjusting member (115) in said opposite rotational direction upon movement of said dose adjusting member (15) from its distal end position to its proximal end position, at least while said guide member (67) is freely rotatable relative to the housing.

6. The injection device of claim 1, further including at least one elastically deformable element (63, 64) located between the guide member (67) and said dose-adjusting member (15); and wherein said at least one elastically deformable element is positively coupled to at least one of; said guide member (67) and said dose-adjusting member (15).

7. The injection device of claim 1, wherein the guide member (16) is provided with at least one engagement element (72), which engagement element, in the proximal end position of said dose-adjusting member (15), is in engagement with at least one further engagement element (93) of the injection device, said further engagement element being substantially complementary with said at least one engagement element (72) and is structurally connected to the housing.

8. The injection device of claim 7, wherein the engagement element (72) of the guide member (67) comprises a first set of longitudinally extending teeth (72);

said at least one further engagement element (93) comprises a corresponding second set of longitudinally extending teeth (93), said second set of teeth (93) being structurally connected to the housing (100) and operatively associated with said first set of teeth for engagement with said first set of teeth at least in the proximal end position of said dose-adjusting member (15).

9. The injection device of claim 8, wherein said retaining means comprises a pawl (118) and ratchet teeth (42), said retaining means being arranged between said housing (100) and said dose-adjusting member (15), said pawl (118) engaging said ratchet teeth (42) in the distal end position of said dose-adjusting member; and wherein the first set of said longitudinally extending teeth (72) has a tooth pitch angle (α) compatible with said ratchet teeth (42).

10. The injection device of claim 9, wherein the tooth pitch of the ratchet teeth (42) and the tooth pitch of the first set of longitudinally extending teeth (72) have respective values such that the larger value can be divided integrally by a smaller value.

11. The injection device of claim 9, wherein the teeth of the first set of longitudinally extending teeth (72) are angularly aligned with said retaining means to permit, upon movement of said dose-adjusting member (15) from its distal end position to its proximal end position, substantially rotation-free linear motion of the dose-adjusting member (15) and of the guide member (67).

12. The injection device of claim 1, wherein the threaded spindle (19) is made of plastic material and has longitudinal grooves (29, 30) formed thereon, disposed symmetrically with respect to one another; and wherein the guide member (67) includes a guide element (69) in engagement with at least one of said longitudinal grooves (29, 30).

13. The injection device of claim 1, wherein the threaded spindle (19) is subdivided longitudinally into two visually distinguishable regions (24, 25).

14. The injection device of claim 13, wherein one region (25) of the threaded spindle is colored.

15. The injection device of claim 1, wherein the guide member is positioned for direct contact with at least one of said cartridge (11) and a cartridge holder (148, 162) receiving the cartridge; and wherein said guide member (67) guides at least one of the cartridge (11) or the cartridge holder (148, 162) for proximal movement during an injection process, to thereby move said cartridge or said cartridge holder, respectively, in proximal direction.

16. The injection device of claim 1, further including an actuation device (38) located outside of said housing (100); and wherein said dose-adjusting member (15) is coupled to said actuation device (38) for movement, by said actuation device, of said dose-adjusting member from its proximal end position to its distal end position, for tensioning said spring means (53), and for preselecting a desired injection dose when said dose-adjusting member (15) is in the distal end position.

17. The injection device of claim 16, further including a releasable detent device (59, 104), couple with said dose-adjusting member (15) for locking said dose-adjusting member (15) into place when said dose-adjusting member is in the distal end position.

18. An injection device for injecting fluid into a subject, comprising a housing (100);

at least one of a cartridge holder (148, 162) and a liquid-containing cartridge (11) axially movable with said housing, said liquid-containing cartridge having a proximal end portion shaped and dimensioned to receive an injection needle (74) coupled thereto;

spring means (53), for storing energy needed to perform an injection, located in said housing (100), said spring means having one end portion thereof operatively coupled to one of said cartridge and said cartridge holder, and another end portion connected to said housing (100);

retaining means for retaining said spring means (53) in an energy-storing position;

injection-starting means for starting an injection, said injection-starting means including first means for releasing, after start of an injection, a first portion of the energy stored in said spring means, and for transferring said released energy to at least one of said cartridge and said cartridge holder, for moving at least one of said cartridge and said cartridge holder, and the injection needle (74) coupled to said cartridge, in a subject-proximal direction without pressing liquid out of the cartridge; and second means for subsequently releasing a second portion of the energy stored in said spring means (53) when a predetermined axial position, with respect to said housing, of at least one of said cartridge and said cartridge holder is reached during said movement of at least one of said cartridge and said cartridge holder in the subject-proximal direction for then pressing liquid out of said cartridge and through the injection needle coupled to said cartridge.

19. The injection device of claim 18, wherein said spring means (53) is a coil spring (53) which stores a portion of its energy by axial compression, and another portion of the energy by torsional stressing.

20. The injection device of claim 19, wherein said first portion of the energy stored in said coil spring (53) and released to move at least one of said cartridge and said cartridge holder and said needle coupled to said cartridge (11) comprises energy stored in said coil spring by axial compression; and wherein said second part of the energy stored in said coil spring (53) and released during injection of liquid out of said cartridge (11) comprises energy stored by torsional stressing.

21. The injection device of claim 18, wherein said device further comprises a dose-adjusting member (15) axially movable within said housing (100) between two end positions, and formed with an internal thread;

a threaded spindle (19) guided in the thread (17) of said dose-adjusting member (15);

and wherein said first means for releasing a first portion of the energy includes means for converting the first portion of the energy stored in said spring means into subject-proximal movement of said dose-adjusting member (15), and means for transferring said proximal movement to at least one of the cartridge and the cartridge holder for moving at least one of the cartridge and the cartridge holder in subject-proximal direction; and wherein said second means includes means enabled by said proximal movement of the at least one of the cartridge and the cartridge holder for converting said second portion of the energy stored in said second portion of the energy stored in said spring means (53) into rotation of said dose-adjusting member relative to said threaded spindle, said threaded spindle pressing liquid out of said cartridge (11) loaded by axial movement of said threaded spindle.

22. The injection device of claim 21, further including rotation-disabling means coupled to said threaded spindle, for disabling rotation of said threaded spindle relative to said housing when said dose-adjusting member is in a subject-proximal end position.

23. The injection device of claim 21, further including rotation-enabling means coupled to said threaded spindle to enable rotation of said threaded spindle relative to said housing when said dose-adjusting member is in a subject remote or distal end position.

* * * * *